United States Patent
Zhang

(10) Patent No.: US 10,406,373 B2
(45) Date of Patent: Sep. 10, 2019

(54) NOISE DETECTION AND FREQUENCY DETERMINATION IN AN EXTRA-CARDIOVASCULAR IMPLANTABLE CARDIOVERTER DEFIBRILLATOR SYSTEM

(71) Applicant: Medtronic, Inc., Minneapolis, MN (US)

(72) Inventor: Xusheng Zhang, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 107 days.

(21) Appl. No.: 15/416,461

(22) Filed: Jan. 26, 2017

(65) Prior Publication Data

US 2018/0207436 A1 Jul. 26, 2018

(51) Int. Cl.
*A61N 1/362* (2006.01)
*A61N 1/39* (2006.01)
*A61B 5/0464* (2006.01)
*A61B 5/04* (2006.01)
*A61N 1/37* (2006.01)
*A61N 1/365* (2006.01)

(52) U.S. Cl.
CPC ........ *A61N 1/3925* (2013.01); *A61B 5/04017* (2013.01); *A61B 5/0464* (2013.01); *A61N 1/3718* (2013.01); *A61N 1/3956* (2013.01); *A61N 1/3987* (2013.01); *A61N 1/365* (2013.01); *A61N 1/3621* (2013.01)

(58) Field of Classification Search
CPC .. A61N 1/3621; A61N 1/3718; A61N 1/3925; A61N 1/3956; A61B 5/04017; A61B 5/0464
See application file for complete search history.

(56) References Cited

U.S. PATENT DOCUMENTS

| | | | |
|---|---|---|---|
| 5,188,117 A | 2/1993 | Steinhaus et al. | |
| 5,354,316 A | 10/1994 | Keimel | |
| 5,391,192 A * | 2/1995 | Lu | A61N 1/365 600/510 |
| 5,545,186 A | 8/1996 | Olson et al. | |
| 5,647,379 A | 7/1997 | Meltzer | |
| 5,766,227 A | 6/1998 | Nappholz et al. | |
| 6,112,119 A | 8/2000 | Schuelke et al. | |

(Continued)

FOREIGN PATENT DOCUMENTS

EP 2004045 A2 12/2008

OTHER PUBLICATIONS (PCT/US2018/014617) PCT Notification of Transmittal of the International Search Report and the Written Opinion of the International Searching Authority, dated Mar. 13, 2018, 12 pages.

(Continued)

*Primary Examiner* — Eric D. Bertram

(57) ABSTRACT

An extra-cardiovascular implantable cardioverter defibrillator is configured to store a cardiac signal segment in response to sensing a cardiac event and obtain a notch filtered signal segment by notch filtering the cardiac signal segment. The ICD determines a count of crossings of the notch filtered signal segment by the cardiac signal segment and determines whether electromagnetic interference (EMI) is present in the cardiac signal segment based on a value of the count.

30 Claims, 13 Drawing Sheets

(56) References Cited

U.S. PATENT DOCUMENTS

| | | |
|---|---|---|
| 6,393,316 B1 | 5/2002 | Gillberg et al. |
| 6,424,234 B1 | 7/2002 | Stevenson |
| 7,031,771 B2 | 4/2006 | Brown et al. |
| 7,403,813 B1 | 7/2008 | Farazzi et al. |
| 7,496,409 B2 | 2/2009 | Greenhut et al. |
| 7,567,835 B2 | 7/2009 | Gunderson et al. |
| 7,623,913 B2 | 11/2009 | Phillips |
| 7,715,906 B2 | 5/2010 | Krause et al. |
| 7,734,333 B2 | 6/2010 | Ghanem et al. |
| 7,734,336 B2 | 6/2010 | Ghanem et al. |
| 7,742,812 B2 | 6/2010 | Ghanem et al. |
| 7,761,142 B2 | 7/2010 | Ghanem et al. |
| 7,761,150 B2 | 7/2010 | Ghanem et al. |
| 7,769,452 B2 | 8/2010 | Ghanem et al. |
| 7,894,894 B2 | 2/2011 | Stadler et al. |
| 7,904,153 B2 | 3/2011 | Greenhut et al. |
| 7,907,993 B2 | 3/2011 | Ghanem et al. |
| 7,941,214 B2 | 5/2011 | Kleckner et al. |
| 7,991,471 B2 | 8/2011 | Ghanem et al. |
| 8,068,901 B2 | 11/2011 | Ghanem et al. |
| 8,150,514 B2 | 4/2012 | Mollerus |
| 8,160,684 B2 | 4/2012 | Ghanem et al. |
| 8,306,618 B2 | 11/2012 | Ghanem et al. |
| 8,435,185 B2 | 5/2013 | Ghanem et al. |
| 8,437,842 B2 | 5/2013 | Zhang et al. |
| 8,548,573 B2 | 10/2013 | Keefe |
| 8,694,097 B2 | 4/2014 | Cao et al. |
| 8,744,555 B2 | 6/2014 | Allavatam et al. |
| 8,744,556 B2 | 6/2014 | Mahajan et al. |
| 8,825,145 B1 | 9/2014 | Zhang |
| 8,868,170 B2 | 10/2014 | Bonan et al. |
| 8,983,586 B2 | 3/2015 | Zhang |
| 9,026,198 B2 | 5/2015 | Lian et al. |
| 9,174,062 B2 | 11/2015 | Stadler et al. |
| 2002/0026224 A1 | 2/2002 | Thompson et al. |
| 2004/0199082 A1* | 10/2004 | Ostroff ............... A61N 1/37 600/509 |
| 2007/0156190 A1 | 7/2007 | Cinbis |
| 2007/0233198 A1 | 10/2007 | Ghanem et al. |
| 2007/0239046 A1 | 10/2007 | Ghanem et al. |
| 2010/0312131 A1 | 12/2010 | Naware et al. |
| 2011/0184297 A1* | 7/2011 | Vitali ............... A61B 5/04017 600/509 |
| 2011/0196247 A1* | 8/2011 | Cao ............... A61B 5/0464 600/509 |
| 2015/0230723 A1 | 8/2015 | Stadler et al. |
| 2015/0272460 A1 | 10/2015 | Stadler et al. |
| 2015/0306375 A1 | 10/2015 | Marshall et al. |
| 2015/0306410 A1 | 10/2015 | Marshall et al. |
| 2016/0158567 A1 | 6/2016 | Marshall et al. |

OTHER PUBLICATIONS

Zhang et al., "System and Method for Sensing and Detection in an Extra-Cardiovascular Implantable Cardioverter Defibrillator", U.S. Appl. No. 15/140,802, filed Apr. 28, 2016, 77 pages.

Greenhut et al., "Cardiac Electrical Signal Noise Detection for Tachyarrhythmia Episode Rejection", U.S. Appl. No. 62/367,170, filed Jul. 27, 2016, 94 pages.

Zhang et al., "Cardiac Electrical Signal Gross Morphology-Based Noise Detection for Rejection of Ventricular Tachyarrhythmia Detection", U.S. Appl. No. 62/367,166, filed Jul. 27, 2016, 93 pages.

Cao et al., "Cardiac Electrical Signal Morphology and Pattern-Based T-Wave Oversensing Rejection", U.S. Appl. No. 62/367,1221, filed Jul. 27, 2016, 92 pages.

Cao et al., "Multi-Threshold Sensing of Cardiac Electrical Signals in an Extracardiovascular Implantable Cardioverter Defibrillator", U.S. Appl. No. 15/142,171, filed Apr. 29, 2016, 71 pages.

* cited by examiner

NOISE DETECTION AND FREQUENCY DETERMINATION IN AN EXTRA-CARDIOVASCULAR IMPLANTABLE CARDIOVERTER DEFIBRILLATOR SYSTEM

TECHNICAL FIELD

The disclosure relates generally to an extra-cardiovascular implantable cardioverter defibrillator (ICD) system and method for detecting electromagnetic interference (EMI) in a cardiac electrical signal.

BACKGROUND

Medical devices, such as cardiac pacemakers and implantable cardioverter defibrillators (ICDs), provide therapeutic electrical stimulation to a heart of a patient via electrodes carried by one or more medical electrical leads and/or electrodes on a housing of the medical device. The electrical stimulation may include signals such as pacing pulses or cardioversion or defibrillation shocks. In some cases, a medical device may sense cardiac electrical signals attendant to the intrinsic or pacing-evoked depolarizations of the heart and control delivery of stimulation signals to the heart based on sensed cardiac electrical signals. Upon detection of an abnormal rhythm, such as bradycardia, tachycardia or fibrillation, an appropriate electrical stimulation signal or signals may be delivered to restore or maintain a more normal rhythm of the heart. For example, an ICD may deliver pacing pulses to the heart of the patient upon detecting bradycardia or tachycardia or deliver cardioversion or defibrillation shocks to the heart upon detecting tachycardia or fibrillation. The ICD may sense the cardiac electrical signals in a heart chamber and deliver electrical stimulation therapies to the heart chamber using electrodes carried by transvenous medical electrical leads. Cardiac signals sensed within the heart generally have a high signal strength and quality for reliably sensing cardiac electrical events, such as R-waves. In other examples, a non-transvenous lead may be coupled to the ICD, in which case cardiac signal sensing presents new challenges in accurately sensing cardiac electrical events.

SUMMARY

In general, the disclosure is directed to techniques for detecting EMI in a cardiac electrical signal received by an implantable medical device, such as an extra-cardiovascular ICD. In some examples, an extracardiovascular ICD system operating according to the techniques disclosed herein includes a notch filter for filtering a cardiac electrical signal to establish a noise threshold. EMI may be detected based on crossings of the noise threshold by the cardiac electrical signal. The ICD may withhold a tachyarrhythmia detection and/or tachyarrhythmia therapy when EMI is detected.

In one example, the disclosure provides an extra-cardiovascular ICD including a therapy delivery circuit configured to deliver a tachyarrhythmia therapy to a patient's heart via extra-cardiovascular electrodes; a sensing circuit configured to receive a cardiac electrical signal via an extra-cardiovascular sensing electrode vector and sense a cardiac event in response to the cardiac electrical signal crossing a sensing threshold amplitude; a memory; and a control circuit coupled to the sensing circuit, the therapy delivery circuit and the memory. The control circuit is configured to store a cardiac signal segment in the memory in response to the sensing circuit sensing the cardiac event, obtain a notch filtered signal segment by notch filtering the cardiac signal segment, determine a count of crossings of the notch filtered signal segment by the cardiac signal segment, determine whether EMI is present in the cardiac signal segment based on a value of the count, and withhold a tachyarrhythmia therapy in response to determining that EMI is present.

In another example, the disclosure provides a method performed by an extra-cardiovascular ICD including receiving a cardiac electrical signal via an extra-cardiovascular sensing electrode vector by a sensing circuit of the ICD, sensing a cardiac event by the sensing circuit in response to the cardiac electrical signal crossing a sensing threshold amplitude, storing a cardiac signal segment in memory of the ICD in response to the sensing circuit sensing the cardiac event, and obtaining a notch filtered signal segment by notch filtering the cardiac signal segment. The method further includes determining a count of crossings of the notch filtered signal segment by the cardiac signal segment, determining whether EMI is present in the cardiac signal segment based on a value of the count, and withholding a tachyarrhythmia therapy in response to determining that EMI is present.

In another example, the disclosure provides a non-transitory, computer-readable storage medium comprising a set of instructions which, when executed by a control circuit of an extra-cardiovascular ICD, cause the extra-cardiovascular ICD to receive a cardiac electrical signal via an extra-cardiovascular sensing electrode vector by a sensing circuit of the ICD, sense a cardiac event by the sensing circuit in response to the cardiac electrical signal crossing a sensing threshold amplitude, store a cardiac signal segment in memory of the ICD in response to the sensing circuit sensing the cardiac event, obtain a notch filtered signal segment by notch filtering the cardiac signal segment, and determine a count of crossings of the notch filtered signal segment by the cardiac signal segment. The ICD is further caused to determine whether electromagnetic interference EMI is present in the cardiac signal segment based on a value of the count and withhold a tachyarrhythmia therapy in response to determining that EMI is present.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

DETAILED DESCRIPTION

In general, this disclosure describes techniques for detecting noise contamination of a cardiac electrical signal in an implantable medical device system, which may be an extra-cardiovascular ICD system, and withholding detection of a tachyarrhythmia in response to detecting noise. As used herein, the term "extra-cardiovascular" refers to a position outside the blood vessels, heart, and pericardium surrounding the heart of a patient. Implantable electrodes carried by extra-cardiovascular leads may be positioned extra-thoracically (outside the ribcage and sternum) or intra-thoracically (beneath the ribcage or sternum) but generally not in intimate contact with myocardial tissue. The techniques disclosed herein provide a method for detecting EMI in a cardiac electrical signal acquired using extra-cardiovascular electrodes and withholding detection of tachyarrhythmia, e.g., ventricular tachycardia (VT) and ventricular fibrillation (VF), when EMI is detected. The EMI is detected using a noise threshold that is established by notch filtering a cardiac electrical signal and comparing a segment of the cardiac electrical signal to the noise threshold.

The techniques are described in conjunction with a system including an implantable sub-sternal or supra-sternal medical lead carrying extra-cardiovascular electrodes, but aspects disclosed herein may be utilized in conjunction with other cardiac electrical sensing lead and electrode systems. For example, the techniques for detecting EMI as described in conjunction with the accompanying drawings may be implemented in any implantable or external medical device enabled for sensing cardiac electrical signals, including implantable pacemakers, ICDs or cardiac monitors coupled to transvenous or epicardial leads carrying sensing electrodes; leadless pacemakers, ICDs or cardiac monitors having housing-based sensing electrodes; and external pacemakers, defibrillators, or cardiac monitors coupled to external, surface or skin electrodes.

Figure 1A:
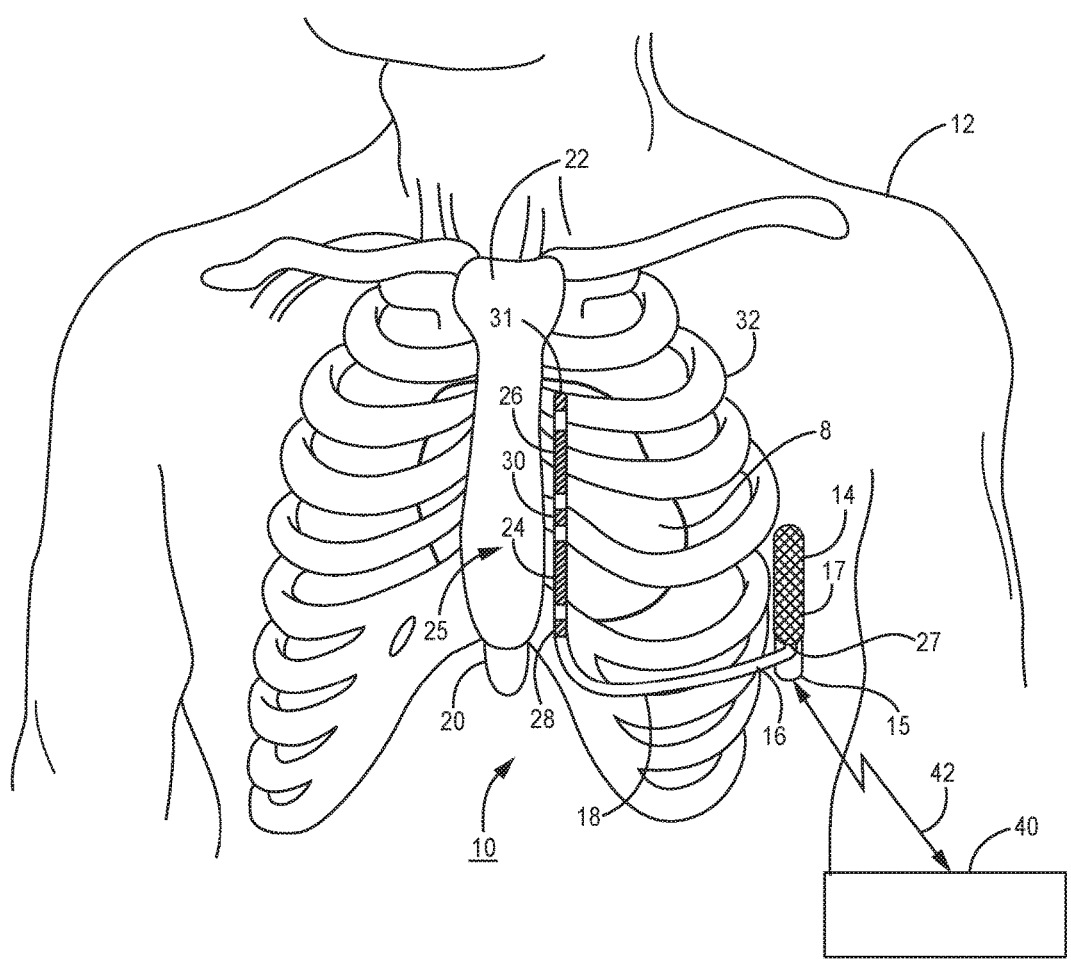
FIGS. 1A and 1B are conceptual diagrams of an extra-cardiovascular ICD system according to one example.
Figure 1B:
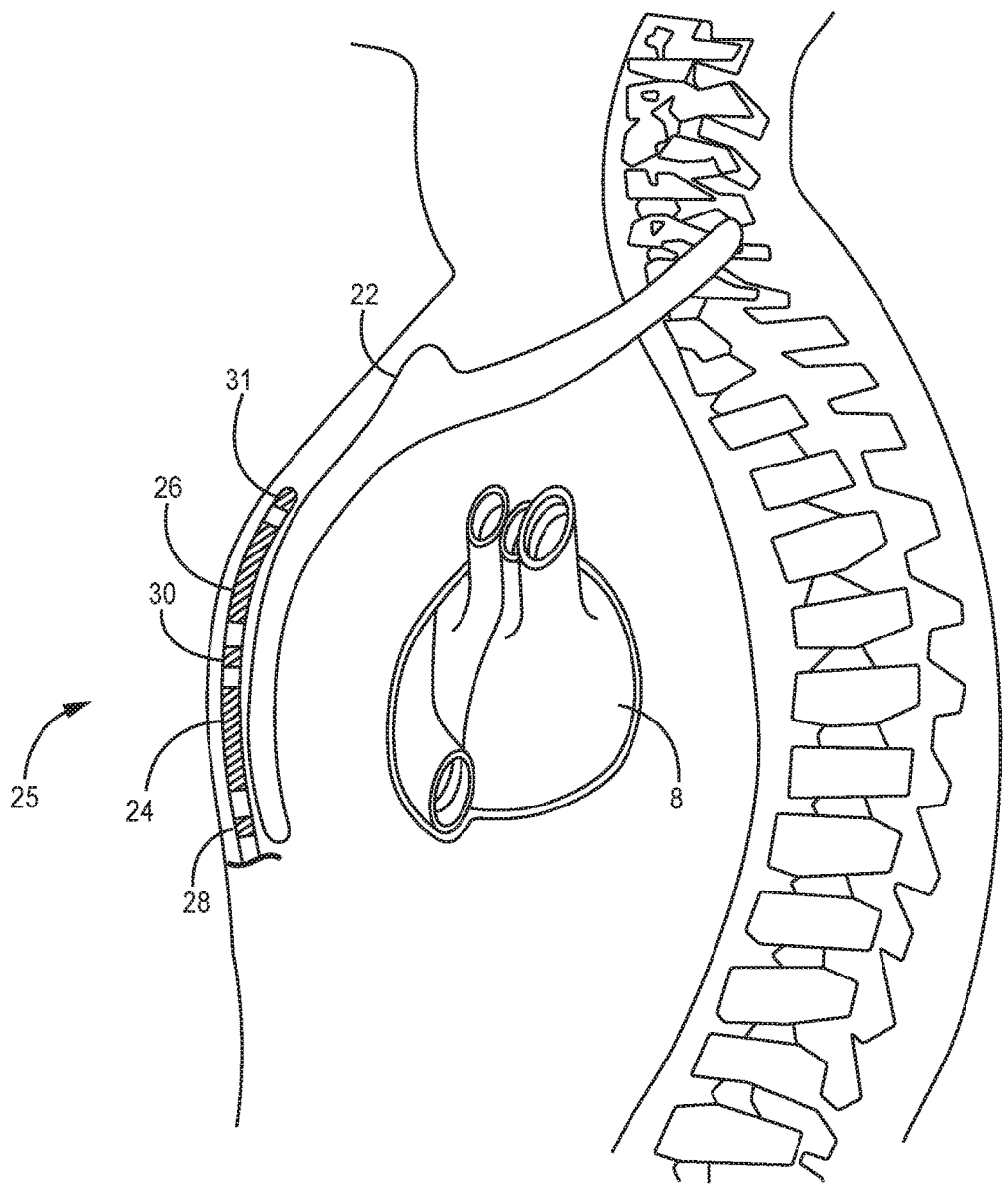

FIGS. 1A and 1B are conceptual diagrams of an extra-cardiovascular ICD system 10 according to one example. FIG. 1A is a front view of ICD system 10 implanted within patient 12. FIG. 1B is a side view of ICD system 10 implanted within patient 12. ICD system 10 includes an ICD 14 connected to an extra-cardiovascular electrical stimulation and sensing lead 16. FIGS. 1A and 1B are described in the context of an ICD system 10 capable of providing defibrillation and/or cardioversion shocks and pacing pulses.

ICD 14 includes a housing 15 that forms a hermetic seal that protects internal components of ICD 14. The housing 15 of ICD 14 may be formed of a conductive material, such as titanium or titanium alloy. The housing 15 may function as an electrode (sometimes referred to as a "can" electrode). Housing 15 may be used as an active can electrode for use in delivering cardioversion/defibrillation (CV/DF) shocks or other high voltage pulses delivered using a high voltage therapy circuit. In other examples, housing 15 may be available for use in delivering unipolar, low voltage cardiac pacing pulses in conjunction with lead-based cathode electrodes and for sensing cardiac electrical signals in conjunction with lead-based electrodes. In other instances, the housing 15 of ICD 14 may include a plurality of electrodes on an outer portion of the housing. The outer portion(s) of the housing 15 functioning as an electrode(s) may be coated with a material, such as titanium nitride.

ICD 14 includes a connector assembly 17 (also referred to as a connector block or header) that includes electrical feedthroughs crossing housing 15 to provide electrical connections between conductors extending within the lead body 18 of lead 16 and electronic components included within the housing 15 of ICD 14. As will be described in further detail herein, housing 15 may house one or more processors, memories, transceivers, electrical cardiac signal sensing circuitry, therapy delivery circuitry, power sources and other components for sensing cardiac electrical signals, detecting a heart rhythm, and controlling and delivering electrical stimulation pulses to treat an abnormal heart rhythm.

Elongated lead body 18 has a proximal end 27 that includes a lead connector (not shown) configured to be connected to ICD connector assembly 17 and a distal portion 25 that includes one or more electrodes. In the example illustrated in FIGS. 1A and 1B, the distal portion 25 of lead body 18 includes defibrillation electrodes 24 and 26 and pace/sense electrodes 28, 30 and 31. In some cases, defibrillation electrodes 24 and 26 may together form a defibrillation electrode in that they may be configured to be activated concurrently. Alternatively, defibrillation electrodes 24 and 26 may form separate defibrillation electrodes in which case each of the electrodes 24 and 26 may be activated independently.

Electrodes 24 and 26 (and in some examples housing 15) are referred to herein as defibrillation electrodes because they are utilized, individually or collectively, for delivering high voltage stimulation therapy (e.g., cardioversion or defibrillation shocks). Electrodes 24 and 26 may be elongated coil electrodes and generally have a relatively high surface area for delivering high voltage electrical stimulation pulses compared to pacing and sensing electrodes 28, 30 and 31. However, electrodes 24 and 26 and housing 15 may also be utilized to provide pacing functionality, sensing functionality or both pacing and sensing functionality in addition to or instead of high voltage stimulation therapy. In this sense, the use of the term "defibrillation electrode" herein should not be considered as limiting the electrodes 24 and 26 for use in only high voltage cardioversion/defibrillation shock therapy applications. For example, electrodes 24 and 26 may be used in a sensing vector used to sense cardiac electrical signals and detect VT and VF.

Electrodes 28, 30 and 31 are relatively smaller surface area electrodes which are available for use in sensing electrode vectors for sensing cardiac electrical signals and may be used for delivering low voltage pacing pulses in some configurations. Electrodes 28, 30 and 31 are referred to as pace/sense electrodes because they are generally configured for use in low voltage applications, e.g., used as either a cathode or anode for delivery of pacing pulses and/or sensing of cardiac electrical signals. In some instances, electrodes 28, 30 and 31 may provide only pacing functionality, only sensing functionality or both.

ICD 14 may obtain cardiac electrical signals corresponding to electrical activity of heart 8 via a combination of sensing vectors that include combinations of electrodes 28, 30, and/or 31. In some examples, housing 15 of ICD 14 is used in combination with one or more of electrodes 28, 30 and/or 31 in a sensing electrode vector. ICD 14 may even obtain cardiac electrical signals using a sensing vector that includes one or both defibrillation electrodes 24 and/or 26, e.g., between electrodes 24 and 26 or one of electrodes 24 or 26 in combination with one or more of electrodes 28, 30, 31, and/or the housing 15. Various sensing electrode vectors utilizing combinations of electrodes 24, 26, 28, 30 and 31 and housing 15 are described below for acquiring first and second cardiac electrical signals using first and second sensing electrode vectors, respectively, selected by sensing circuitry including in ICD 14.

In the example illustrated in FIGS. 1A and 1B, electrode 28 is located proximal to defibrillation electrode 24, and electrode 30 is located between defibrillation electrodes 24 and 26. A third pace/sense electrode 31 may be located distal to defibrillation electrode 26. Electrodes 28 and 30 are illustrated as ring electrodes, and electrode 31 is illustrated as a hemispherical tip electrode in the example of FIGS. 1A and 1B. However, electrodes 28, 30 and 31 may comprise any of a number of different types of electrodes, including ring electrodes, short coil electrodes, hemispherical electrodes, directional electrodes, segmented electrodes, or the like, and may be positioned at any position along the distal portion 25 of lead 16 and are not limited to the positions shown. Further, electrodes 28, 30 and 31 may be of similar type, shape, size and material or may differ from each other.

Lead 16 extends subcutaneously or submuscularly over the ribcage 32 medially from the connector assembly 27 of ICD 14 toward a center of the torso of patient 12, e.g., toward xiphoid process 20 of patient 12. At a location near xiphoid process 20, lead 16 bends or turns and extends superior subcutaneously or submuscularly over the ribcage and/or sternum, substantially parallel to sternum 22. Although illustrated in FIGS. 1A and 1B as being offset laterally from and extending substantially parallel to sternum 22, lead 16 may be implanted at other locations, such as over sternum 22, offset to the right or left of sternum 22, angled laterally from sternum 22 toward the left or the right, or the like. Alternatively, lead 16 may be placed along other subcutaneous or submuscular paths. The path of extra-cardiovascular lead 16 may depend on the location of ICD 14, the arrangement and position of electrodes carried by the lead distal portion 25, and/or other factors.

Electrical conductors (not illustrated) extend through one or more lumens of the elongated lead body 18 of lead 16 from the lead connector at the proximal lead end 27 to electrodes 24, 26, 28, 30 and 31 located along the distal portion 25 of the lead body 18. Lead body 18 may be tubular or cylindrical in shape. In other examples, the distal portion 25 (or all of) the elongated lead body 18 may have a flat, ribbon or paddle shape. The lead body 18 of lead 16 may be formed from a non-conductive material, including silicone, polyurethane, fluoropolymers, mixtures thereof, and other appropriate materials, and shaped to form one or more lumens within which the one or more conductors extend. However, the techniques disclosed herein are not limited to such constructions or to any particular lead body design.

The elongated electrical conductors contained within the lead body 18 are each electrically coupled with respective defibrillation electrodes 24 and 26 and pace/sense electrodes 28, 30 and 31, which may be separate respective insulated conductors within the lead body. The respective conductors electrically couple the electrodes 24, 26, 28, 30 and 31 to circuitry, such as a therapy delivery circuit and/or a sensing circuit, of ICD 14 via connections in the connector assembly 17, including associated electrical feedthroughs crossing housing 15. The electrical conductors transmit therapy from a therapy delivery circuit within ICD 14 to one or more of defibrillation electrodes 24 and 26 and/or pace/sense electrodes 28, 30 and 31 and transmit sensed electrical signals from one or more of defibrillation electrodes 24 and 26 and/or pace/sense electrodes 28, 30 and 31 to the sensing circuit within ICD 14.

ICD 14 analyzes the cardiac electrical signals received from one or more of the sensing electrode vectors to monitor for abnormal rhythms, such as bradycardia, VT or VF. ICD 14 may analyze the heart rate and/or morphology of the cardiac electrical signals to monitor for tachyarrhythmia in accordance with any of a number of tachyarrhythmia detection techniques. One example technique for detecting tachyarrhythmia is described in U.S. Pat. No. 7,761,150 (Ghanem, et al.), incorporated by reference herein in its entirety.

ICD 14 generates and delivers electrical stimulation therapy in response to detecting a tachyarrhythmia (e.g., VT or VF). ICD 14 may deliver ATP in response to VT detection, and in some cases may deliver ATP prior to a CV/DF shock or during high voltage capacitor charging in an attempt to avert the need for delivering a CV/DF shock. ATP may be delivered using an extra-cardiovascular pacing electrode vector selected from any of electrodes 24, 26, 28, 30, 31 and/or housing 15. The pacing electrode vector may be different than the sensing electrode vector. If ATP does not successfully terminate VT or when VF is detected, ICD 14 may deliver one or more cardioversion or defibrillation (CV/DF) shocks via one or both of defibrillation electrodes 24 and 26 and/or housing 15. ICD 14 may deliver the CV/DF shocks using electrodes 24 and 26 individually or together as a cathode (or anode) and with the housing 15 as an anode (or cathode). ICD 14 may generate and deliver other types of electrical stimulation pulses such as post-shock pacing pulses or bradycardia pacing pulses using a pacing electrode vector that includes one or more of the electrodes 24, 26, 28, 30 and 31 and the housing 15 of ICD 14.

FIGS. 1A and 1B are illustrative in nature and should not be considered limiting of the practice of the techniques disclosed herein. In other examples, lead 16 may include less than three pace/sense electrodes or more than three pace/sense electrodes and/or a single defibrillation electrode or more than two electrically isolated or electrically coupled defibrillation electrodes or electrode segments. The pace/sense electrodes 28, 30 and/or 31 may be located elsewhere along the length of lead body 18. For example, lead 16 may include a single pace/sense electrode 30 between defibrillation electrodes 24 and 26 and no pace/sense electrodes distal to defibrillation electrode 26 or proximal defibrillation electrode 24. Various example configurations of extra-cardiovascular leads and electrodes and dimensions that may be implemented in conjunction with the EMI detection techniques disclosed herein are described in pending U.S. Publication No. 2015/0306375 (Marshall, et al.) and pending U.S. Publication No. 2015/0306410 (Marshall, et al.), both of which are incorporated herein by reference in their entirety.

ICD 14 is shown implanted subcutaneously on the left side of patient 12 along the ribcage 32. ICD 14 may, in some instances, be implanted between the left posterior axillary line and the left anterior axillary line of patient 12. ICD 14 may, however, be implanted at other subcutaneous or submuscular locations in patient 12. For example, ICD 14 may be implanted in a subcutaneous pocket in the pectoral region. In this case, lead 16 may extend subcutaneously or submuscularly from ICD 14 toward the manubrium of sternum 22 and bend or turn and extend inferiorly from the manubrium to the desired location subcutaneously or submuscularly. In yet another example, ICD 14 may be placed abdominally. Lead 16 may be implanted in other extracardiovascular locations as well. For instance, as described with respect to FIGS. 2A-2C, the distal portion 25 of lead 16 may be implanted underneath the sternum/ribcage in the substernal space.

An external device 40 is shown in telemetric communication with ICD 14 by a communication link 42. External device 40 may include a processor, display, user interface, telemetry unit and other components for communicating with ICD 14 for transmitting and receiving data via communication link 42. Communication link 42 may be established between ICD 14 and external device 40 using a radio frequency (RF) link such as BLUETOOTH®, Wi-Fi, or Medical Implant Communication Service (MICS) or other RF or communication frequency bandwidth.

External device 40 may be embodied as a programmer used in a hospital, clinic or physician's office to retrieve data from ICD 14 and to program operating parameters and algorithms in ICD 14 for controlling ICD functions. External device 40 may be used to program cardiac event sensing parameters (e.g., R-wave sensing parameters), cardiac rhythm detection parameters (e.g., VT and VF detection parameters) and therapy control parameters used by ICD 14. Data stored or acquired by ICD 14, including physiological signals or associated data derived therefrom, results of device diagnostics, and histories of detected rhythm episodes and delivered therapies, may be retrieved from ICD 14 by external device 40 following an interrogation command. External device 40 may alternatively be embodied as a home monitor or hand held device.

Figure 2A:
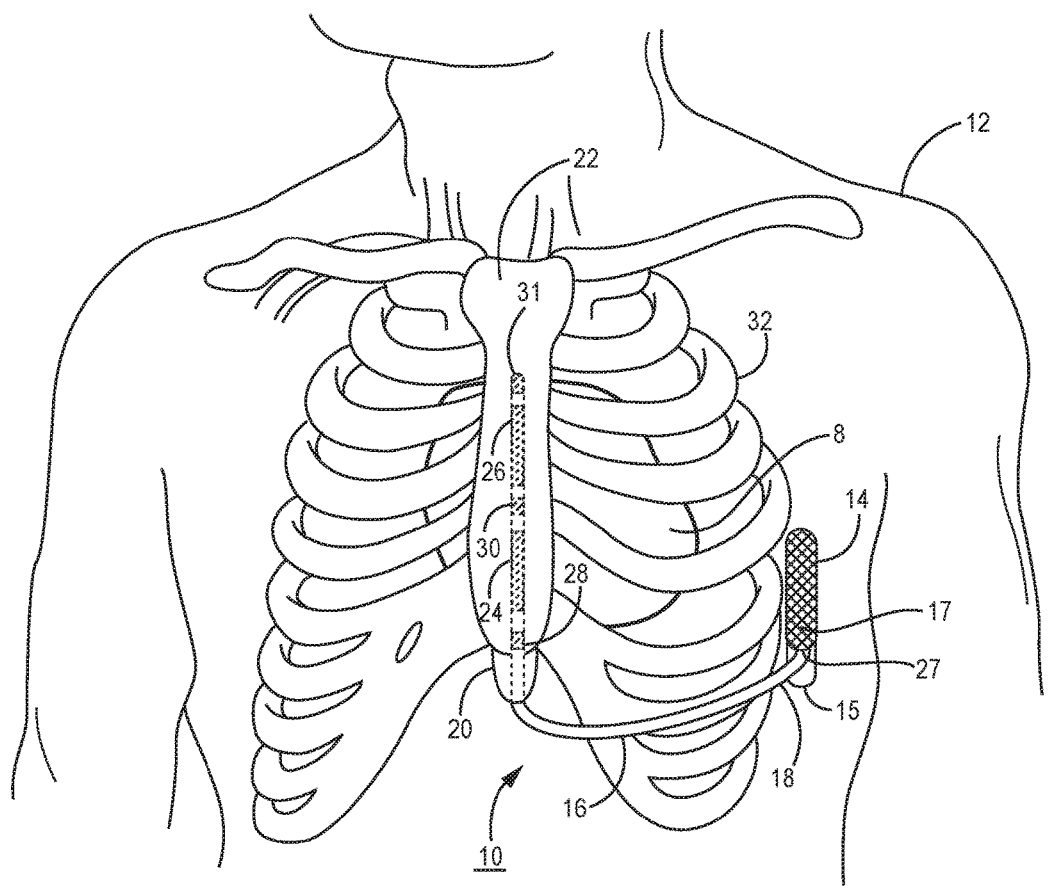
FIGS. 2A-2C are conceptual diagrams of a patient implanted with the extra-cardiovascular ICD system of FIG. 1A in a different implant configuration.
Figure 2B:
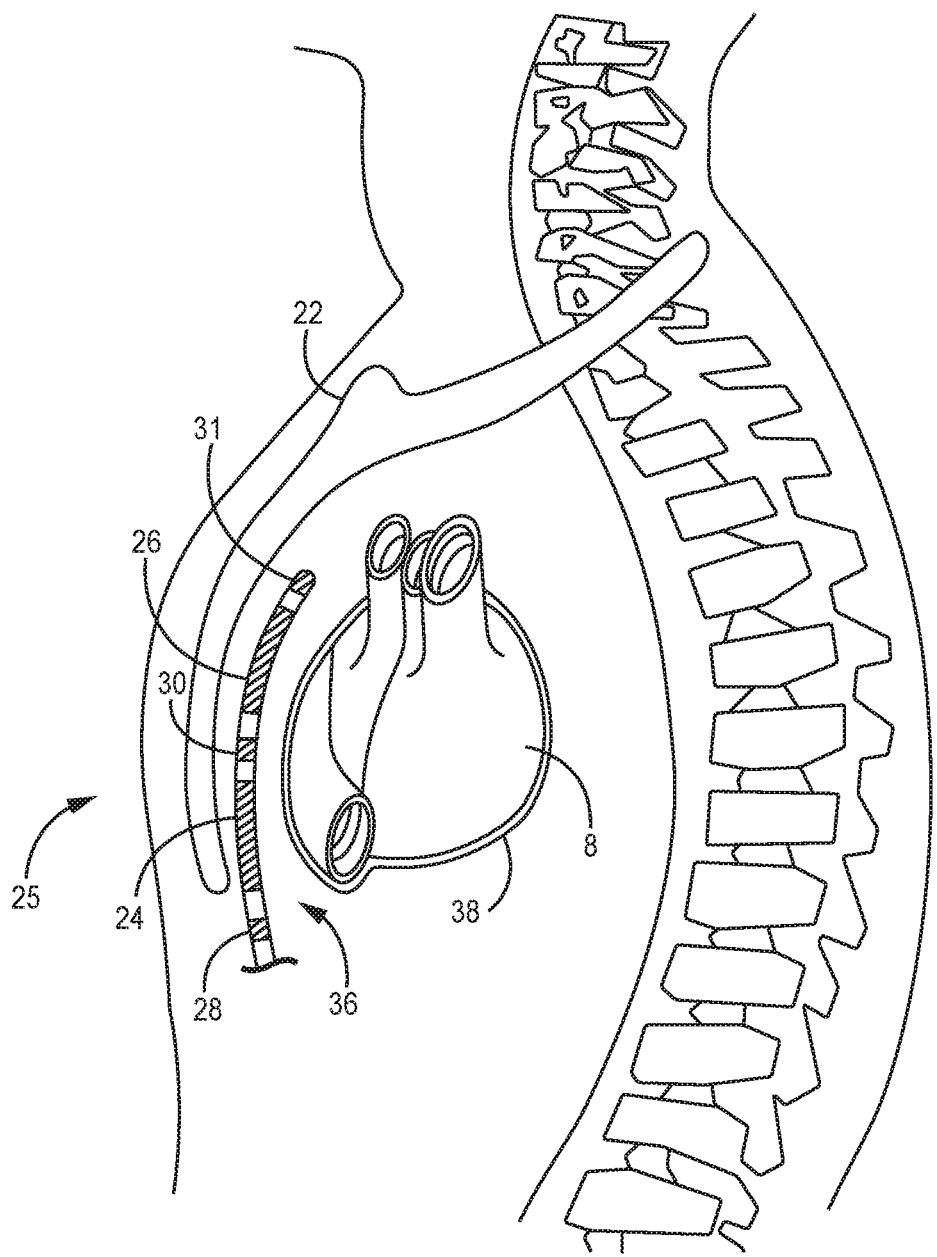
Figure 2C:
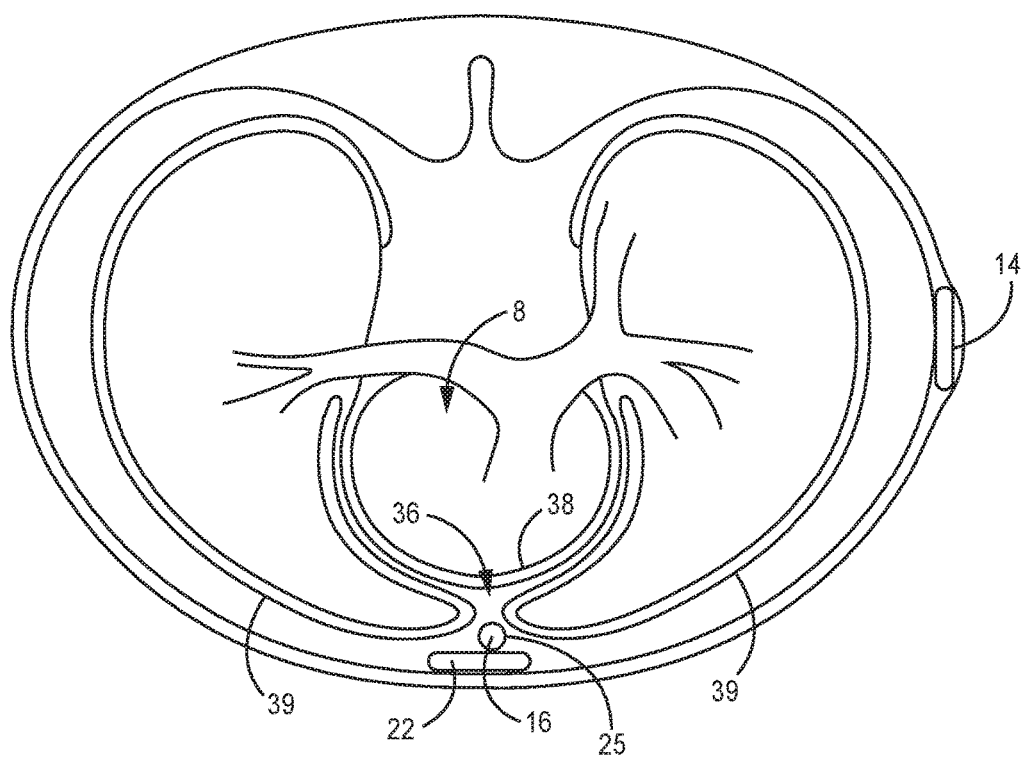

FIGS. 2A-2C are conceptual diagrams of patient 12 implanted with extra-cardiovascular ICD system 10 in a different implant configuration than the arrangement shown in FIGS. 1A-1B. FIG. 2A is a front view of patient 12 implanted with ICD system 10. FIG. 2B is a side view of patient 12 implanted with ICD system 10. FIG. 2C is a transverse view of patient 12 implanted with ICD system 10. In this arrangement, extra-cardiovascular lead 16 of system 10 is implanted at least partially underneath sternum 22 of patient 12. Lead 16 extends subcutaneously or submuscularly from ICD 14 toward xiphoid process 20 and at a location near xiphoid process 20 bends or turns and extends superiorly within anterior mediastinum 36 in a substernal position.

Anterior mediastinum 36 may be viewed as being bounded laterally by pleurae 39, posteriorly by pericardium 38, and anteriorly by sternum 22 (see FIG. 2C). The distal portion 25 of lead 16 may extend along the posterior side of sternum 22 substantially within the loose connective tissue and/or substernal musculature of anterior mediastinum 36. A lead implanted such that the distal portion 25 is substantially within anterior mediastinum 36, may be referred to as a "substernal lead."

In the example illustrated in FIGS. 2A-2C, lead 16 is located substantially centered under sternum 22. In other instances, however, lead 16 may be implanted such that it is offset laterally from the center of sternum 22. In some instances, lead 16 may extend laterally such that distal portion 25 of lead 16 is underneath/below the ribcage 32 in addition to or instead of sternum 22. In other examples, the distal portion 25 of lead 16 may be implanted in other extra-cardiovascular, intra-thoracic locations, including the pleural cavity or around the perimeter of and adjacent to but typically not within the pericardium 38 of heart 8. Other implant locations and lead and electrode arrangements that may be used in conjunction with the EMI detection techniques described herein are generally disclosed in the above-incorporated references.

Figure 3:
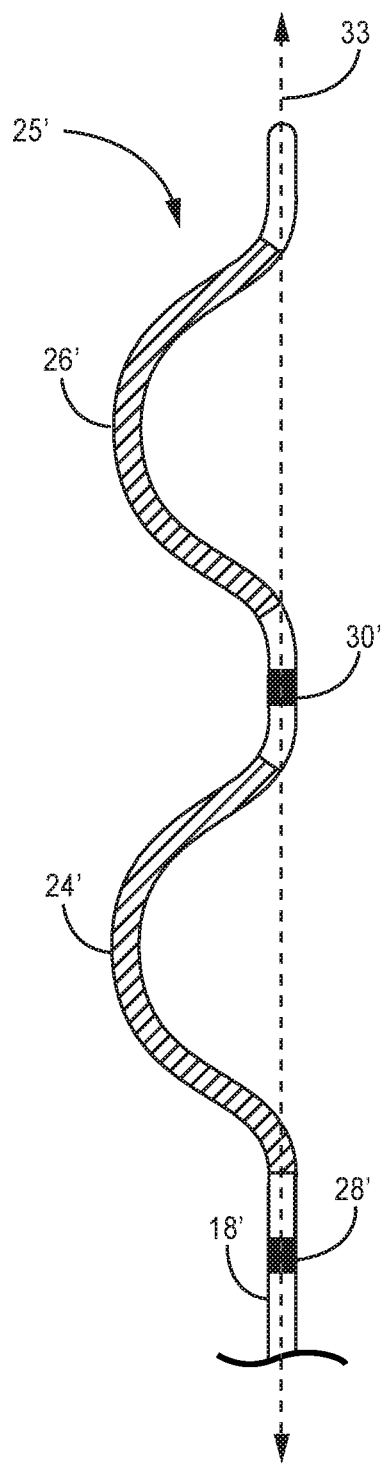
FIG. 3 is a conceptual diagram of a distal portion of an extra-cardiovascular lead having an electrode configuration according to another example.

FIG. 3 is a conceptual diagram illustrating a distal portion 25' of another example of extra-cardiovascular lead 16 of FIGS. 1A-2C having a curving distal portion 25' of lead body 18'. Lead body 18' may be formed having a curving, bending, serpentine, undulating or zig-zagging shape along distal portion 25'. In the example shown, defibrillation electrodes 24' and 26' are carried along curving portions of the lead body 18'. Pace/sense electrode 30' is carried in between defibrillation electrodes 24' and 26'. Pace/sense electrode 28' is carried proximal to the proximal defibrillation electrode 24'. No electrode is provided distal to defibrillation electrode 26' in this example.

As shown in FIG. 3, lead body 18' may be formed having a curving distal portion 25' that includes two "C" shaped curves, which together may resemble the Greek letter epsilon, "ε." Defibrillation electrodes 24' and 26' are each carried by one of the two respective C-shaped portions of the lead body distal portion 25', which extend or curve in the same direction away from a central axis 33 of lead body 18'. In the example shown, pace/sense electrode 28' is proximal to the C-shaped portion carrying electrode 24', and pace/sense electrode 30' is proximal to the C-shaped portion carrying electrode 26'. Pace/sense electrodes 28' and 30' may, in some instances, be approximately aligned with the central axis 33 of the straight, proximal portion of lead body 18' such that mid-points of defibrillation electrodes 24' and 26' are laterally offset from electrodes 28' and 30'. Other examples of extra-cardiovascular leads including one or more defibrillation electrodes and one or more pacing and sensing electrodes carried by curving, serpentine, undulating or zig-zagging distal portion of the lead body that may be implemented with the pacing techniques described herein are generally disclosed in pending U.S. Pat. Publication No. 2016/0158567 (Marshall, et al.), incorporated herein by reference in its entirety.

Figure 4:
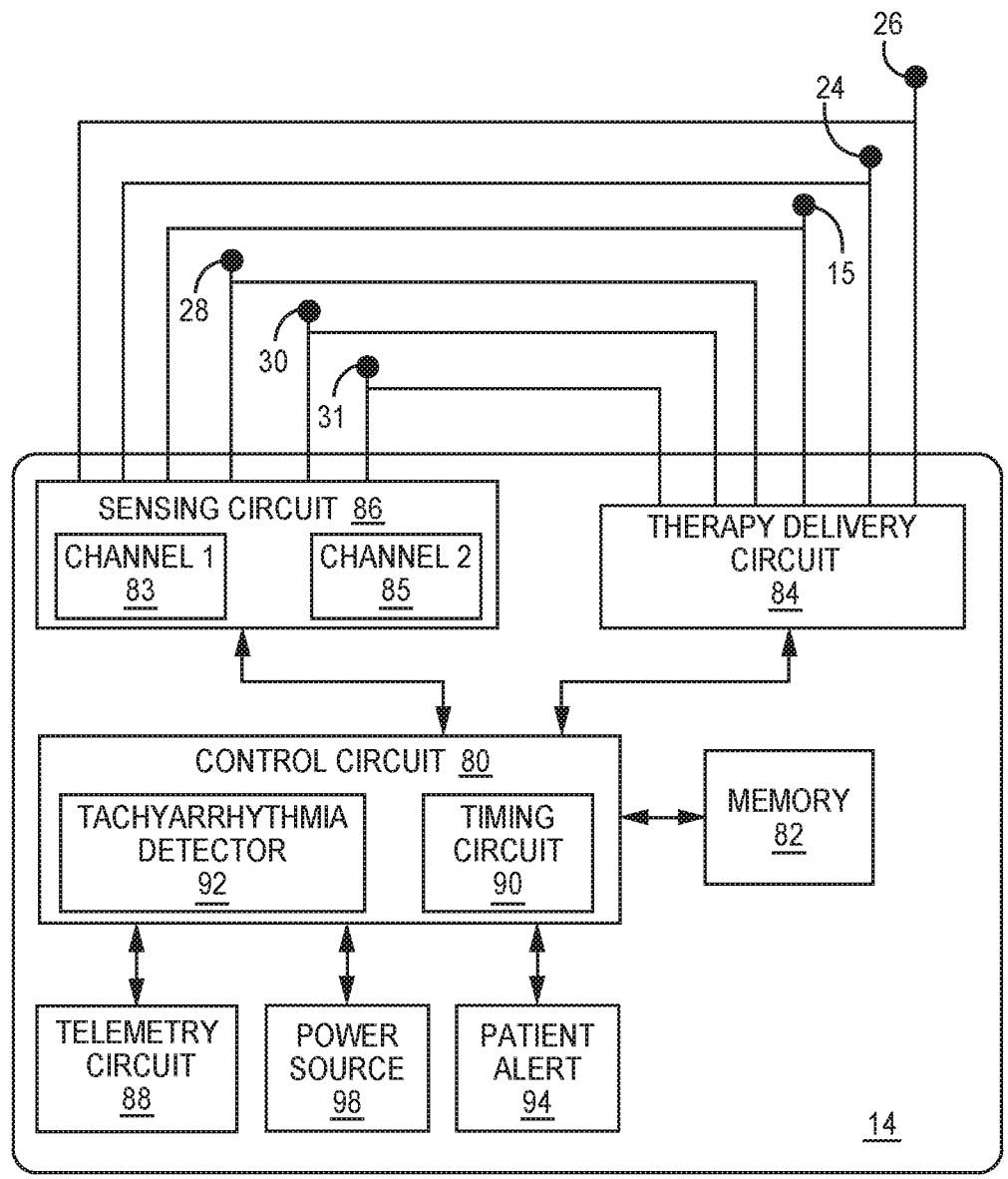
FIG. 4 is a schematic diagram of the ICD of FIGS. 1A-2C according to one example.

FIG. 4 is a schematic diagram of ICD 14 according to one example. The electronic circuitry enclosed within housing 15 (shown schematically as an electrode in FIG. 4) includes software, firmware and hardware that cooperatively monitor cardiac electrical signals, determine when an electrical stimulation therapy is necessary, and deliver therapies as needed according to programmed therapy delivery algorithms and control parameters. The software, firmware and hardware are configured to detect tachyarrhythmias and deliver anti-tachyarrhythmia therapy, e.g., detect ventricular tachyarrhythmias and in some cases discriminate VT from VF for determining when ATP or CV/DF shocks are required. ICD 14 is coupled to an extra-cardiovascular lead, such as lead 16 carrying extra-cardiovascular electrodes 24, 26, 28, 30 and 31 (if present), for delivering electrical stimulation pulses to the patient's heart and for sensing cardiac electrical signals.

ICD 14 includes a control circuit 80, memory 82, therapy delivery circuit 84, sensing circuit 86, and telemetry circuit 88 and may include a patient alert circuit 94 in some examples. A power source 98 provides power to the circuitry of ICD 14, including each of the components 80, 82, 84, 86, 88 and 94 as needed. Power source 98 may include one or more energy storage devices, such as one or more rechargeable or non-rechargeable batteries. The connections between power source 98 and each of the other components 80, 82, 84, 86 and 88 are to be understood from the general block diagram of FIG. 4, but are not shown for the sake of clarity. For example, power source 98 may be coupled to one or more charging circuits included in therapy delivery circuit 84 for charging holding capacitors included in therapy delivery circuit 84 that are discharged at appropriate times under the control of control circuit 80 for producing electrical pulses according to a therapy protocol, such as for bradycardia pacing, post-shock pacing, ATP and/or CV/DF shock pulses. Power source 98 is also coupled to components of sensing circuit 86, such as sense amplifiers, analog-to-digital converters, switching circuitry, etc. as needed.

The circuits and components shown in FIG. 4 represent functionality included in ICD 14 and each may include one or more discrete and/or integrated electronic circuit components that implement analog and/or digital circuits capable of producing the functions attributed to ICD 14 herein. The various circuits and components may include an application specific integrated circuit (ASIC), an electronic circuit, a processor (shared, dedicated, or group) and memory that execute one or more software or firmware programs, a combinational logic circuit, state machine, or other suitable components or combinations of components that provide the described functionality. The particular form of software, hardware and/or firmware employed to implement the functionality disclosed herein will be determined primarily by the particular system architecture employed in the ICD and by the particular detection and therapy delivery methodologies employed by the ICD. Providing software, hardware, and/or firmware to accomplish the described functionality in the context of any modern ICD system, given the disclosure herein, is within the abilities of one of skill in the art. Functionality associated with one or more components may be performed by separate hardware, firmware or software components or integrated within common hardware, firmware or software components. For example, cardiac event sensing may be performed by sensing circuit 86 under the control of control circuit 80 and may include operations implemented in a processor or other signal processing circuitry included in control circuit 80 executing instructions stored in memory 82 and control signals such as blanking and timing intervals and sensing threshold amplitude signals sent from control circuit 80 to sensing circuit 86.

Memory 82 may include any volatile, non-volatile, magnetic, or electrical non-transitory computer readable storage media, such as random access memory (RAM), read-only memory (ROM), non-volatile RAM (NVRAM), electrically-erasable programmable ROM (EEPROM), flash memory, or any other memory device. Furthermore, memory 82 may include non-transitory computer readable media storing instructions that, when executed by one or more processing circuits, cause control circuit 80 and/or other ICD components to perform various functions attributed to ICD 14 or those ICD components. The non-transitory computer-readable media storing the instructions may include any of the media listed above.

Control circuit 80 communicates, e.g., via a data bus, with therapy delivery circuit 84 and sensing circuit 86 for sensing cardiac electrical activity, detecting cardiac rhythms, and controlling delivery of cardiac electrical stimulation therapies in response to sensed cardiac signals. Control circuit 80 may include a microprocessor-based controller that employs digital signal analysis techniques to characterize the digitized signals stored in memory 82 to recognize and classify the patient's heart rhythm employing any of numerous signal processing methodologies for analyzing cardiac signals and cardiac event waveforms, e.g., R-waves. Examples of devices and algorithms that may be adapted to utilize techniques for EMI detection described herein are generally disclosed in U.S. Pat. No. 5,354,316 (Keimel); U.S. Pat. No. 5,545,186 (Olson, et al.); U.S. Pat. No. 6,393,316 (Gillberg et al.); U.S. Pat. No. 7,031,771 (Brown, et al.); U.S. Pat. No. 8,160,684 (Ghanem, et al.), and U.S. Pat. No. 8,437,842 (Zhang, et al.), all of which patents are incorporated herein by reference in their entirety.

Therapy delivery circuit 84 and sensing circuit 86 are electrically coupled to electrodes 24, 26, 28, 30 and 31 (if present as shown in FIGS. 1A and 2A) carried by lead 16 (e.g., as shown in FIGS. 1A-3) and the housing 15, which may function as a common or ground electrode or as an active can electrode for delivering CV/DF shock pulses or cardiac pacing pulses. Sensing circuit 86 may be selectively coupled to electrodes 28, 30, 31 and/or housing 15 in order to monitor electrical activity of the patient's heart. Sensing circuit 86 may additionally be selectively coupled to defibrillation electrodes 24 and/or 26 for use in a sensing electrode vector. Sensing circuit 86 may be enabled to selectively receive cardiac electrical signals from at least two sensing electrode vectors from the available electrodes 24, 26, 28, 30, 31 and housing 15. At least two cardiac electrical signals from two different sensing electrode vectors may be received simultaneously by sensing circuit 86, and sensing circuit 86 may monitor one or both or the cardiac electrical signals at a time for sensing cardiac electrical events. For example, sensing circuit 86 may include switching circuitry for selecting which of electrodes 24, 26, 28, 30, 31 and housing 15 are coupled to other components or circuits of sensing circuit 86. Switching circuitry may include a switch array, switch matrix, multiplexer, or any other type of switching device suitable to selectively couple components of sensing circuit 86 to selected electrodes.

In some examples, sensing circuit 86 includes multiple sensing channels 83 and 85 for acquiring cardiac electrical signals from multiple sensing vectors selected from electrodes 24, 26, 28, 30, 31 and housing 15 via the switching circuitry. Each sensing channel 83 and 85 may be configured to amplify, filter and digitize the cardiac electrical signal received from selected electrodes coupled to the respective sensing channel to improve the signal quality for detecting cardiac events, such as R-waves or performing other signal analysis. The cardiac event detection circuitry within sensing circuit 86 may include one or more sense amplifiers, filters, rectifiers, threshold detectors, comparators, analog-to-digital converters (ADCs), timers or other analog or digital components as described further in conjunction with FIG. 5. A cardiac event sensing threshold may be automatically adjusted by sensing circuit 86 under the control of control circuit 80, based on timing intervals and sensing threshold values determined by control circuit 80, stored in memory 82, and/or controlled by hardware, firmware and/or software of control circuit 80 and/or sensing circuit 86. As disclosed herein, the first sensing channel 83 may be configured to sense cardiac events such as R-waves based on a cardiac event sensing threshold, and the second sensing channel 85 may be configured to pass a digitized cardiac electrical signal obtained from a different sensing electrode vector to control circuit 80 for use in confirming a cardiac event sensed by first sensing channel 83.

Upon sensing a cardiac event based on a sensing threshold crossing, first sensing channel 83 may produce a sensed event signal, such as an R-wave sensed event signal, that is passed to control circuit 80. In some examples, the sensed event signal may be used by control circuit 80 to trigger storage of a segment of the second cardiac electrical signal received by second sensing channel 85 for post-processing and analysis for confirming the R-wave sensed event signal. As described below, the control circuit 80 may be configured to detect EMI from the second cardiac signal segment using a noise threshold established by notch-filtering the second cardiac signal segment.

The R-wave sensed event signals produced by sensing circuit 86 are also used by control circuit 80 for determining RR intervals (RRIs) for detecting tachyarrhythmia and determining a need for therapy. An RRI is the time interval between consecutively sensed R-waves and may be determined between consecutive R-wave sensed event signals received from sensing circuit 86. For example, control circuit 80 may include a timing circuit 90 for determining RRIs between consecutive R-wave sensed event signals received from sensing circuit 86 and for controlling various timers and/or counters used to control the timing of therapy delivery by therapy delivery circuit 84. Timing circuit 90 may additionally set time windows such as morphology template windows, morphology analysis windows or perform other timing related functions of ICD 14 including synchronizing cardioversion shocks or other therapies delivered by therapy delivery circuit 84 with sensed cardiac events.

Memory 82 may include read-only memory (ROM) in which stored programs controlling the operation of the control circuit 80 reside. Memory 82 may further include random access memory (RAM) or other memory devices configured as a number of recirculating buffers capable of holding a series of measured RRIs, counts or other data for analysis by the tachyarrhythmia detector 92. Memory 82 may be configured to store a predetermined number of cardiac electrical signal segments in circulating buffers under the control of control circuit 80, e.g., at least one, two or other number of cardiac electrical signal segments. Each segment may be written to memory 82 over a time interval extending before and after the R-wave sensed event signal produced by the first sensing channel 83. Control circuit 80 may access stored cardiac electrical signal segments when confirmation of R-waves sensed by the first sensing channel 83 is required based on the detection of a predetermined number of tachyarrhythmia intervals, which may precede tachyarrhythmia detection.

When noise, such as EMI is present in the cardiac electrical signal(s) received by sensing circuit 86, false R-wave sensed event signals may be produced and passed to control circuit 80 when EMI noise spikes cross the R-wave sensing threshold. As described below in conjunction with FIG. 5, at least one sensing channel, e.g., sensing channel 85, may include a notch filter for filtering the cardiac electrical signal received by the respective sensing channel 85 in some examples. The notch filtered cardiac electrical signal may be used as a noise threshold by control circuit 80 for detecting EMI in the cardiac electrical signal as described below, e.g., in conjunction with the flow chart of FIG. 8. Based on crossings of the noise threshold by the cardiac electrical signal, a sensed R-wave may be identified as an EMI event. EMI may be detected by control circuit 80 when a threshold number of EMI events are identified. Detection of EMI may cause control circuit 80 to withhold a tachyarrhythmia detection or therapy and/or generate an alert.

For example, tachyarrhythmia detector 92 may compare the RRIs determined by timing circuit 90 to one or more tachyarrhythmia detection interval zones, such as a tachycardia detection interval zone and a fibrillation detection interval zone. RRIs falling into a detection interval zone are counted by a respective VT interval counter or VF interval counter and in some cases in a combined VT/VF interval counter included in tachyarrhythmia detector 92. When an interval counter reaches a detection threshold, a ventricular tachyarrhythmia may be detected by tachyarrhythmia detector 92. Tachyarrhythmia detector 92 may be configured to perform other signal analysis for determining if other detection criteria are satisfied before detecting VT or VF, such as R-wave morphology criteria, onset criteria, and noise and oversensing rejection criteria. Control circuit 80 may withhold a VT or VF detection when an NID is reached by a VT or VF interval counter if EMI is being detected.

Examples of other parameters that may be determined from cardiac electrical signals received by sensing circuit 86 for determining the status of tachyarrhythmia detection rejection rules that may cause withholding to a VT or VF detection are described in provisionally-filed U.S. Patent Application 62/367,166, provisionally-filed U.S. Patent Application 62/367,170, and provisionally-filed U.S. Patent Application 62/367,221, all filed on Jul. 27, 2016, and pending U.S. patent application Ser. No. 15/140,802 (Zhang, et al.), all of which are incorporated herein by reference in their entirety.

To support additional cardiac signal analyses performed by tachyarrhythmia detector 92, sensing circuit 86 may pass a digitized cardiac electrical signal to control circuit 80 for morphology analysis performed by tachyarrhythmia detector 92 for detecting and discriminating heart rhythms. A cardiac electrical signal from the selected sensing vector, e.g., from first sensing channel 83 and/or the second sensing channel 85, may be passed through a filter and amplifier, provided to a multiplexer and thereafter converted to multi-bit digital signals by an analog-to-digital converter, all included in sensing circuit 86, for storage in memory 82.

Therapy delivery circuit 84 includes charging circuitry, one or more charge storage devices such as one or more high voltage capacitors and/or low voltage capacitors, and switching circuitry that controls when the capacitor(s) are discharged across a selected pacing electrode vector or CV/DF shock vector. Charging of capacitors to a programmed pulse amplitude and discharging of the capacitors for a programmed pulse width may be performed by therapy delivery circuit 84 according to control signals received from control circuit 80. Timing circuit 90 of control circuit 80 may include various timers or counters that control when ATP or other cardiac pacing pulses are delivered. For example, timing circuit 90 may include programmable digital counters set by a microprocessor of the control circuit 80 for controlling the basic time intervals associated with various pacing modes or ATP sequences delivered by ICD 14. The microprocessor of control circuit 80 may also set the amplitude, pulse width, polarity or other characteristics of the cardiac pacing pulses, which may be based on programmed values stored in memory 82.

In response to detecting VT or VF, ATP and/or CV/DF therapy may be delivered. ATP therapy can be delivered by loading a regimen from the microprocessor included in control circuit 80 into timing circuit 90 according to the type and rate of tachycardia detected. In response to detecting VT or VF, CV/DF therapy can be delivered by initiate charging of high voltage capacitors via a charging circuit, both included in therapy delivery circuit 84. Charging is controlled by control circuit 80 which monitors the voltage on the high voltage capacitors, which is passed to control circuit 80 via a charging control line. When the voltage reaches a predetermined value set by control circuit 80, a logic signal is generated on a capacitor full line passed to therapy delivery circuit 84, terminating charging. The defibrillation or cardioversion pulse is delivered to the heart under the control of the timing circuit 90 by an output circuit of therapy delivery circuit 84 via a control bus. The output circuit may include an output capacitor through which the charged high voltage capacitor is discharged via switching circuitry, e.g., an H-bridge, which determines the electrodes used for delivering the cardioversion or defibrillation pulse and the pulse wave shape. Therapy delivery and control circuitry generally disclosed in any of the above-incorporated patents may be implemented in ICD 14.

Furthermore it is recognized that the methods disclosed herein may be implemented in an implantable medical device that is used for monitoring cardiac electrical signals by sensing circuit 86 and control circuit 80 without having therapy delivery capabilities or in an implantable medical device that monitors cardiac electrical signals and delivers cardiac pacing therapies by therapy delivery circuit 84, without high voltage therapy capabilities, such as cardioversion/defibrillation shock capabilities.

Control parameters utilized by control circuit 80 for detecting cardiac rhythms and controlling therapy delivery may be programmed into memory 82 via telemetry circuit 88. Telemetry circuit 88 includes a transceiver and antenna for communicating with external device 40 (shown in FIG. 1A) using RF communication as described above. Under the control of control circuit 80, telemetry circuit 88 may receive downlink telemetry from and send uplink telemetry to external device 40. In some cases, telemetry circuit 88 may be used to transmit and receive communication signals to/from another medical device implanted in patient 12.

Control circuit 80 may control telemetry circuit 88 to transmit an EMI alert signal in response to identifying EMI events and updating an EMI index that meets EMI alert criteria. In other examples, ICD 14 may include a patient alert circuit 94 that may be controlled by control circuit 80 to generate an alert signal, such as a vibration or audible tone, which is perceivable by the patient. For example, patient alert 94 may include a vibrating circuit that is activated by control circuit 80 in response to determining that an index of EMI events meets patient alert criteria. The patient may be prospectively instructed to move away from an EMI environment upon perceiving the patient alert. Determining an EMI index and generating an EMI alert by ICD 14 is further described below in conjunction with FIG. 8.

Figure 5:
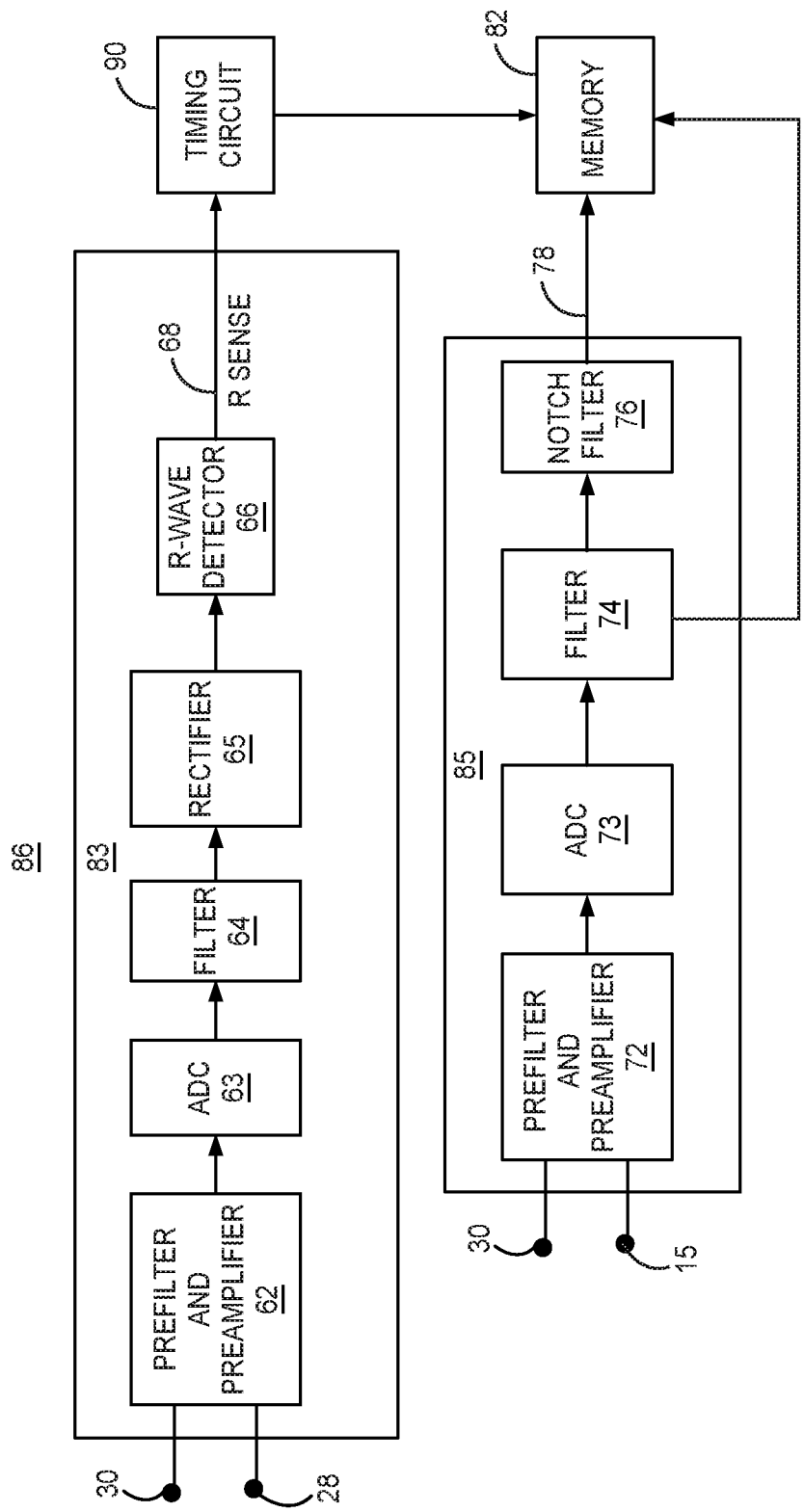
FIG. 5 is diagram of circuitry included in the sensing circuit of FIG. 4 according to one example.

FIG. 5 is a diagram of circuitry included in first sensing channel 83 and second sensing channel 85 of sensing circuit 86 according to one example. First sensing channel 83 may be selectively coupled via switching circuitry (not shown) to a first sensing electrode vector including electrodes carried by extra-cardiovascular lead 16 as shown in FIGS. 1A-2C for receiving a first cardiac electrical signal. First sensing channel 83 may be coupled to a sensing electrode vector that is a short bipole, having a relatively shorter inter-electrode distance or spacing than the second electrode vector coupled to second sensing channel 85. In the example shown, the first sensing electrode vector may include pace/sense electrodes 28 and 30. In other examples, the first sensing electrode vector coupled to sensing channel 83 may include pace/sense electrodes 30 and 31 and in some cases pace/sense electrodes 28 and 31 depending on the inter-electrode spacing and position of the distal portion 25 of lead 16. In some cases, the first sensing channel 83 may be selectively coupled to a sensing electrode vector including a defibrillation electrode 24 and/or 26, e.g., a sensing electrode vector between pace/sense electrode 28 and defibrillation electrode 24, between pace/sense electrode 30 and either of defibrillation electrodes 24 or 26, or between pace/sense electrode 26 and 31. In still other examples, the first sensing electrode vector may be between defibrillation electrodes 24 and 26.

In some patients, a bipole between electrodes carried by lead 16 may result in patient body posture dependent changes in the cardiac electrical signal as the sensing vector of the bipole relative to the cardiac axis changes with changes in patient body posture or body motion. Accordingly, the sensing electrode vector coupled to the first sensing channel 83 may include housing 15 and any of the electrodes 24, 26, 28, 30 and 31 carried by lead 16. A relatively longer bipole including housing 15 and a lead-based electrode may be less sensitive to positional changes but may be more susceptible to EMI. The techniques disclosed herein may be used to detect EMI to avoid oversensing of EMI leading to false detection of VT and VF and unnecessary electrical stimulation therapies.

Sensing circuit 86 includes a second sensing channel 85 that receives a second cardiac electrical signal from a second sensing vector, for example from a vector that includes electrode 30 and housing 15, as shown, or a vector that includes electrode 28 and housing 15. Second sensing channel 85 may be selectively coupled to other sensing electrode vectors, which may form a relatively long bipole having an inter-electrode distance or spacing that is greater than the sensing electrode vector coupled to first sensing channel 83 in some examples. As described below, the second cardiac electrical signal received by second sensing channel 85 via a long bipole may be used by control circuit 80 for EMI detection and signal morphology analysis. In other examples, any vector selected from the available electrodes, e.g., electrodes 24, 26, 28, 30 and/or 31 and/or housing 15 may be included in a sensing electrode vector coupled to second sensing channel 85. The sensing electrode vectors coupled to first sensing channel 83 and second sensing channel 85 are typically different sensing electrode vectors, which may have no common electrodes or only one common electrode but not both.

In the illustrative example shown in FIG. 5, the electrical signals developed across input electrodes 28 and 30 are received by sensing channel 83 and electrical signals developed across electrodes 30 and 15 are received by sensing channel 85. The electrode vectors are shown for the sake of illustration and different sensing vectors may be selectively coupled to sensing channels 83 and 85. The cardiac electrical signals are provided as differential input signals to the pre-filter and pre-amplifiers 62 and 72, respectively, of first sensing channel 83 and second sensing channel 85. Non-physiological high frequency and DC signals may be filtered by a low pass or bandpass filter included in each of pre-filter and pre-amplifiers 62 and 72, and high voltage signals may be removed by protection diodes included in pre-filter and pre-amplifiers 62 and 72. Pre-filter and pre-amplifiers 62 and 72 may amplify the pre-filtered signal by a gain of between 10 and 100, and in one example a gain of 17.5, and may convert the differential signal to a single-ended output signal passed to analog-to-digital converter (ADC) 63 in first sensing channel 83 and to ADC 73 in second sensing channel 85. Pre-filters and amplifiers 62 and 72 may provide anti-alias filtering and noise reduction prior to digitization.

ADC 63 and ADC 73, respectively, convert the first cardiac electrical signal from an analog signal to a first digital bit stream and the second cardiac electrical signal to a second digital bit stream. In one example, ADC 63 and ADC 73 may be sigma-delta converters (SDC), but other types of ADCs may be used. In some examples, the outputs of ADC 63 and ADC 73 may be provided to decimators (not shown), which function as digital low-pass filters that increase the resolution and reduce the sampling rate of the respective first and second cardiac electrical signals.

In sensing channel 83, the digital output of ADC 63 is passed to filter 64 which may be a digital bandpass filter having a bandpass of approximately 10 Hz to 30 Hz for passing cardiac electrical signals such as R-waves typically occurring in this frequency range. The bandpass filtered signal is passed from filter 64 to rectifier 65 then to R-wave detector 66. R-wave detector 66 may include an auto-adjusting sense amplifier, comparator and/or other detection circuitry that compares the filtered and rectified first cardiac electrical signal to an R-wave sensing threshold in real time and produces an R-wave sensed event signal 68 when the cardiac electrical signal crosses the R-wave sensing threshold outside of a post-sense blanking period.

The R-wave sensing threshold, controlled by sensing circuit 86 and/or control circuit 80, may be a multi-level sensing threshold as disclosed in pending U.S. patent application Ser. No. 15/142,171 (Cao, et al., filed on Apr. 29, 2016), incorporated herein by reference in its entirety. Briefly, the multi-level sensing threshold may have a starting sensing threshold value held for a time interval equal to a tachycardia detection interval, then drops to a second sensing threshold value held until a drop time interval expires, which may be 1 to 2 seconds long. The sensing threshold drops to a minimum sensing threshold after the drop time interval. The starting sensing threshold value may be the lower of a predetermined percentage of the most recent, preceding sensed R-wave peak amplitude and a maximum sensing threshold limit determined using a sensitivity-dependent gain and the programmed sensitivity setting. In other examples, the R-wave sensing threshold used by R-wave detector 66 may be set to a starting value based on a preceding R-wave peak amplitude and decay linearly or exponentially over time until reaching a minimum sensing threshold. However, the techniques of this application are not limited to a specific behavior of the sensing threshold. Instead, other decaying, step-wise adjusted or other automatically adjusted sensing thresholds may be utilized.

The second cardiac electrical signal, digitized by ADC 73 of sensing channel 85, may be passed to filter 74 for bandpass filtering. In some examples, filter 74 is a wideband filter for passing frequencies from 1 to 30 Hz or from 1 to 100 Hz. In some examples, sensing channel 85 includes notch filter 76. Notch filter 76 may be implemented in firmware or hardware and is provided to attenuate 50-60 Hz electrical noise, muscle noise, EMI or electrical noise/artifacts in the second cardiac electrical signal. Cardiac electrical signals acquired using extra-cardiovascular electrodes as shown, for example in FIGS. 1A-3, may be more likely to be contaminated by 50-60 Hz electrical noise, muscle noise and other EMI, electrical noise/artifacts than intra-cardiac electrodes. As such, notch filter 76 may be provided to significantly attenuate the magnitude of signals in the range of 50-60 Hz with minimum attenuation of signals in the range of approximately 1-30 Hz, corresponding to typical cardiac electrical signal frequencies.

The output signal 78 of notch filter 76 may be passed from sensing circuit 86 to memory 82 under the control of control circuit 80 for storing segments of the second cardiac electrical signal 78 in temporary buffers of memory 82. For example, timing circuit 90 of control circuit 80 may set a time interval or number of sample points relative to an R-wave sensed event signal 68 received from first sensing channel 83, over which the second cardiac electrical signal 78 is stored in memory 82. The buffered, second cardiac electrical signal segment may be analyzed by control circuit 80 as described in conjunction with FIG. 8, to identify EMI events falsely sensed as R-waves.

Notch filter 76 may be implemented as a digital filter for real-time filtering performed by firmware as part of sensing channel 85 or by control circuit 80 for filtering the buffered digital output of filter 74. In some examples, the output of filter 74 of sensing channel 85 may be stored in memory 82 in time segments defined relative to an R-wave sense event signal 68 prior to filtering by notch filter 76. When control circuit 80 enables EMI detection using buffered second cardiac electrical signal segments, the notch filter 76 may be applied to the stored segment of the second cardiac electrical signal. In this way, if analysis of the buffered signal segments is not required for identifying EMI events, e.g., when the sensed heart rate based on R-wave sensed event signals 68 is relatively slow, firmware implemented to perform the operation of notch filter 76 need not be executed.

The second cardiac electrical signal segments stored in memory 82 may be analyzed for determining if an R-wave sensed by sensing channel 83 that triggered the storage of the second cardiac signal segment is an EMI event. A noise threshold may be established by control circuit 80 by applying notch filter 76 to the second cardiac electrical signal segment to obtain a notch filtered signal segment. A count of positive-going and negative-going crossings of the notch-filtered signal segment may be determined, and the count may be compared to an EMI event threshold. If the EMI event threshold is reached or exceeded, the control circuit 80 may identify the R-wave sensed by first sensing channel 83 as an EMI event and provide a determination of the EMI event to tachyarrhythmia detector 92 for rejecting the sensed cardiac event in a cardiac rhythm determination algorithm as being a noise event or withholding a cardiac rhythm determination. For example, in response to the determination of the R-wave being an EMI event, a tachyarrhythmia detection based on RRIs may be withheld.

The configuration of sensing channels 83 and 85 shown in FIG. 5 is illustrative in nature and should not be considered limiting of the techniques described herein. The sensing channels 83 and 85 of sensing circuit 86 may include more or fewer components than illustrated and described in FIG. 5. As shown, first sensing channel 83 may be configured to detect R-waves in real time, e.g., in hardware implemented components, from a first cardiac electrical signal based on crossings of an R-wave sensing threshold by the first cardiac electrical signal, and second sensing channel 85 may be configured to provide a second cardiac electrical signal for storage in memory 82 for post-processing and analysis by control circuit 80 for confirming R-wave sensed event signals produced by the first sensing channel 83 and identifying EMI events as needed.

In other examples, both sensing channels 83 and 85 may include an R-wave detector for sensing R-waves in real time and producing R-wave sensed event signals and/or both channels 83 and 85 may include a notch filter. Cardiac signal segments may be stored from one or both channels 83 and/or 85 and notch-filtered for establishing a noise threshold that is applied to the respective cardiac signal segment for counting noise threshold crossings and detecting EMI. R-wave sensed event signals produced by a given sensing channel 83 or 85 may be identified as EMI events based on a count of noise threshold crossings during a cardiac signal segment that is obtained from the same sensing channel 83 or 85 or the other sensing channel (85 or 83). For instance, an R-wave sensed by R-wave detector 66 of sensing channel 83 may be identified as EMI event using the techniques described herein applied to a cardiac signal segment obtained from the cardiac signal received by sensing channel 83 from which the R-wave was sensed. In other examples, an R-wave sensed by sensing channel 83 is identified as an EMI event by detecting EMI in a cardiac signal segment obtained by the second sensing channel 85 or vice versa.

The examples described herein generally pertain to R-wave sensing by an extra-cardiovascular ICD, e.g., ICD 14, for determining RRIs in a ventricular tachyarrhythmia detection algorithm. It is to be understood, however, that EMI may be detected in a cardiac electrical signal during P-wave sensing to avoid oversensing of EMI during atrial rhythm detection algorithms. For example, an ICD or other implantable device may be configured for sensing P-waves and detecting atrial tachyarrhythmias. In that case, sensing circuit 86 may be configured with a P-wave detector instead of or in addition to R-wave detector 66.

Figure 6:
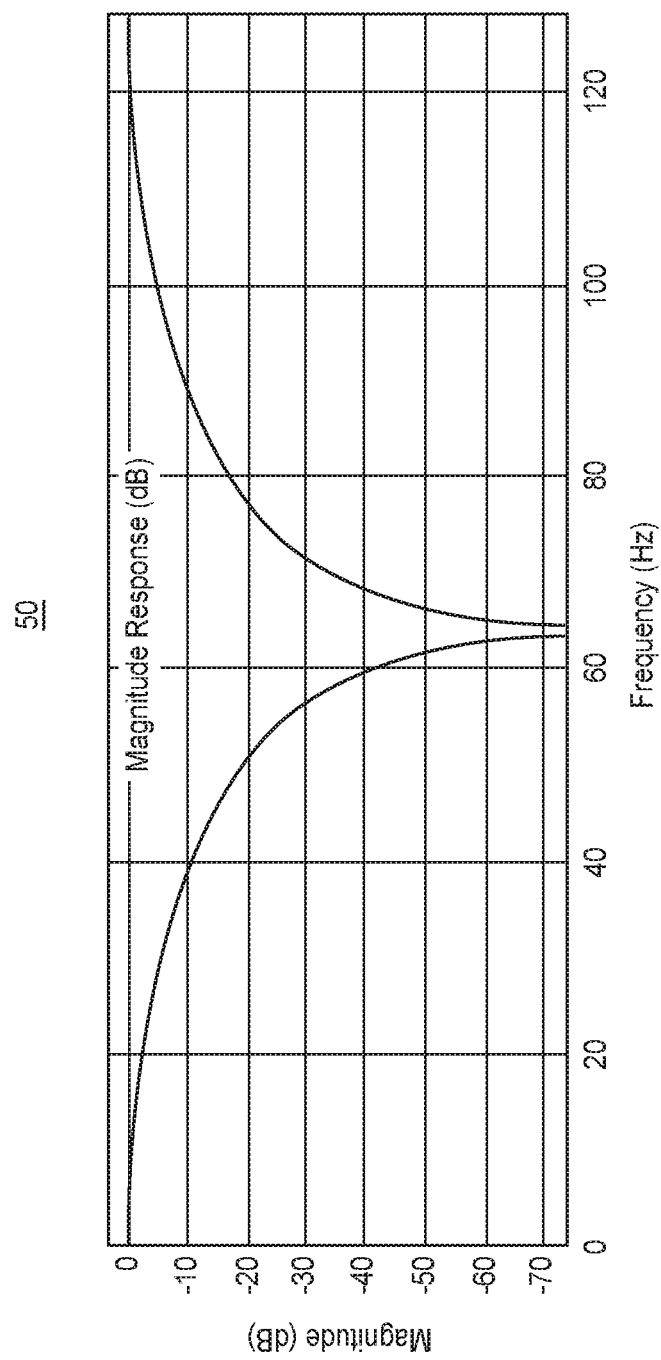
FIG. 6 is a plot of the attenuation characteristics of a notch filter included in the ICD of FIG. 4.

FIG. 6 is a plot 50 of the attenuation characteristics of notch filter 76 of the second sensing channel 85. In one example, notch filter 76 is implemented in firmware as a digital filter. The output of the digital notch filter may be determined by firmware implemented in the second sensing channel 85 according to the equation:

$$Y(n)=(x(n)+2x(n-2)+x(n-4))/4$$

where x(n) is the amplitude of the nth sample point of the digital signal received by the notch filter 76, x(n−2) is the amplitude of the n−2 sample point, and x(n−4) is the amplitude of the n−4 sample point for a sampling rate of 256 Hz. Y(n) is the amplitude of the nth sample point of the notch-filtered, digital second cardiac electrical signal. The plot 50 of FIG. 6 represents the resulting attenuation of the amplitude Y(n) as a function of frequency. At a frequency of 60 Hz, the attenuation of the magnitude of Y(n) is −40 decibels (dB). At a frequency of 50 Hz, the attenuation is −20 dB, and at 23 Hz, which may be typical of an R-wave of the cardiac electrical signal, the attenuation is limited to −3 dB. Notch filter 76 may therefore provide highly attenuated 50 and 60 Hz noise, muscle noise, other EMI, and other electrical noise/artifacts while passing lower frequency cardiac signals in the second cardiac electrical signal output of sensing channel 85. Although the notch filter 76 may not attenuate frequencies approaching the maximum frequency of 128 Hz, filter 74 of second sensing channel 85, which may be a bandpass filter, may adequately reduce the higher frequency range signal content above 60 Hz.

The sample point numbers indicated in the equation above for determining a notch-filtered signal may be modified as needed when a different sampling rate other than 256 Hz is used, however, the resulting frequency response may or may not be the same as that shown in FIG. 6. The notch filter 76 uses few computations. In other examples, other digital filters may be used for attenuation of 50 and 60 Hz. For example, for a sampling rate of 256 Hz, a filtered signal Y(n) may be determined as Y(n)=(x(n)+x(n−1)+x(n−2)+x(n−3))/4 which has less attenuation at 50 and 60 Hz than the frequency response shown in FIG. 6 but acts as a low-pass, notch filter with greater attenuation at higher frequencies (greater than 60 Hz) than the frequency response shown FIG. 6.

Figure 7:
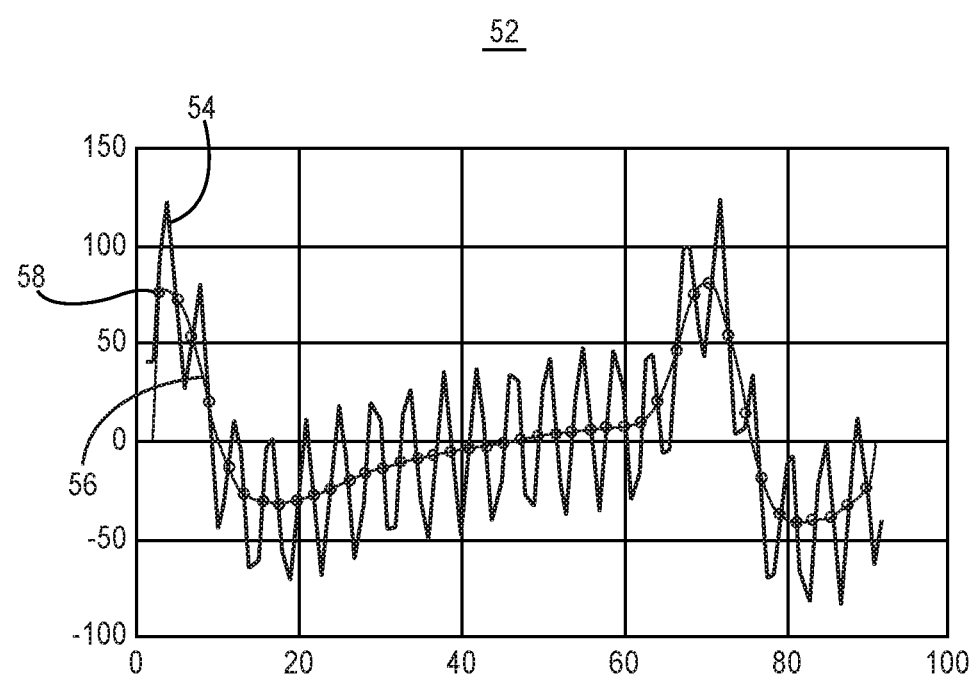
FIG. 7 is a plot of a cardiac signal segment and the notch filtered signal segment.

FIG. 7 is a plot 52 of a cardiac signal segment 54 and the notch filtered signal segment 56. Cardiac signal segment 54 is stored in memory 82 under the control of control circuit 80 in response to an R-wave sensed event signal. The cardiac signal segment 54 may be stored from the second cardiac electrical signal received by second sensing channel 85 in response to an R-wave sensed event signal produced by the first sensing channel 83. In other examples, the stored signal segment 54 may be obtained from the same cardiac electrical signal, e.g., the first cardiac electrical signal, received by sensing channel 83, from which the R-wave is sensed that triggers storage of the cardiac electrical signal segment.

Control circuit 80 may detect and count noise threshold crossings 58 (denoted by circles) by the cardiac signal segment 54. The notch filtered signal segment 56 is determined to establish the noise threshold amplitude. Each crossing 58 of the notch filtered signal segment 56 by the stored cardiac signal segment 54 is counted by control circuit 80. In this example, the cardiac signal segment 54 is sampled at 256 Hz and includes 92 sample points. As described below in conjunction with FIG. 8, the value of the noise threshold crossing count may be compared to an EMI event threshold. The EMI event threshold may be selected based on the number of sample points or duration of the cardiac signal segment 54 and the minimum frequency of EMI that is desired to be detected. If the EMI event threshold is met or exceeded by the noise threshold crossing count, the R-wave sensed event signal that triggered storage of the cardiac electrical signal segment 54 may be identified as an EMI event.

The frequency of EMI may be determined based on the noise threshold crossing count. In some examples, control circuit 80 is configured to determine the frequency of the EMI that led to the R-wave sensed event signal being identified as an EMI event. In the example of FIG. 7, the EMI frequency may be calculated as:

$$\text{EMI Freq}=(\text{SampFreq}/\text{SampNumber})*(\text{Count}/2)$$

where SampFreq is the sampling frequency of the cardiac signal segment 54, SampNumber is the number of sample points included in the cardiac signal segment and Count is the value of the noise threshold crossing count. The noise threshold crossing count is divided by a factor of 2 because both positive-going and negative-going crossings are counted in FIG. 7. In the example of FIG. 7, the cardiac signal segment 54 is not rectified and each cycle crosses the noise threshold twice (positive-going and negative-going). In the example shown, the noise threshold crossing count is 42. Using the above equation, control circuit 80 may determine the EMI frequency to be approximately 60 Hz.

Figure 8:
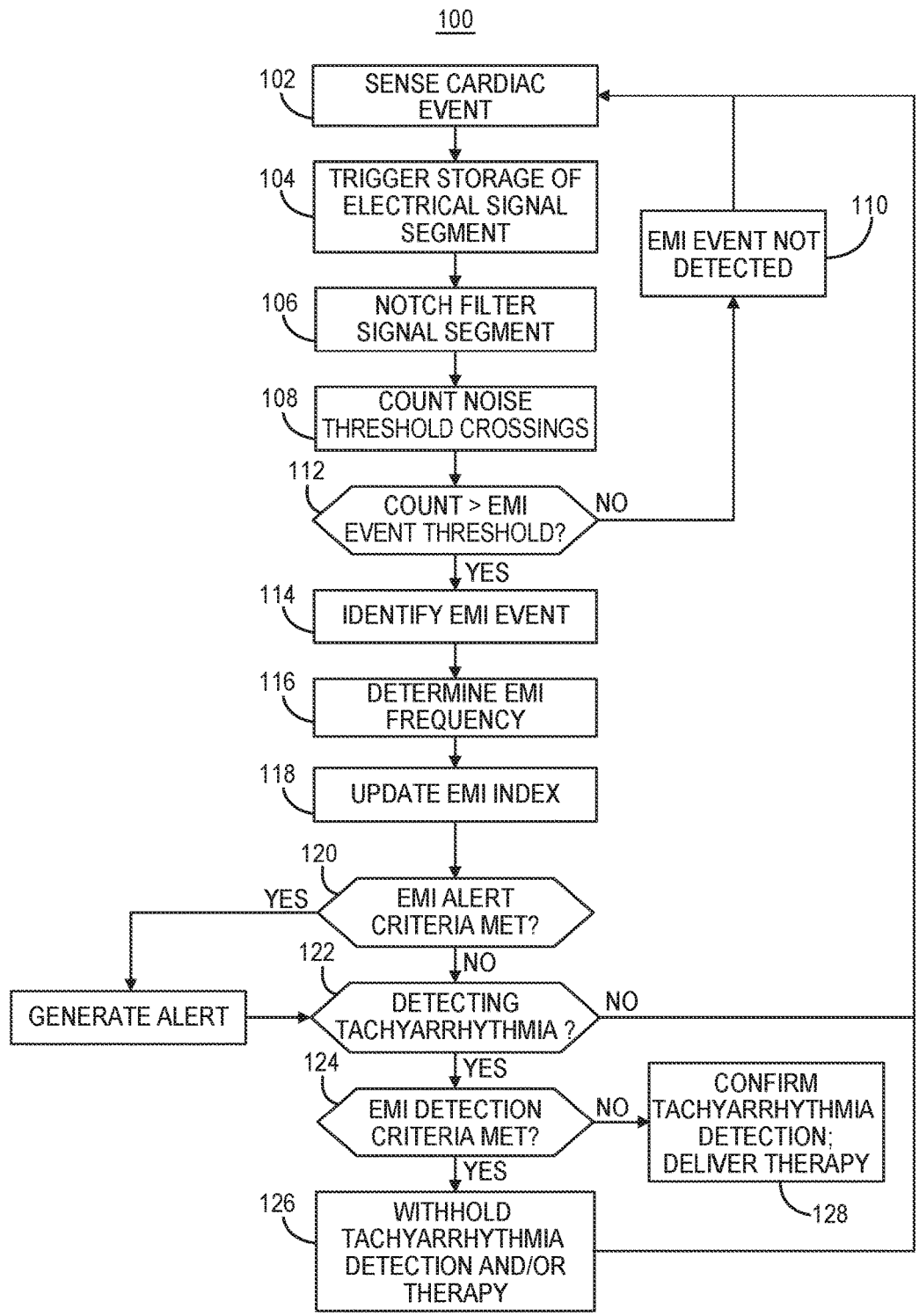
FIG. 8 is a flow chart of a method performed by an ICD for detecting EMI according to one example.

FIG. 8 is a flow chart 100 of a method performed by ICD 14 for detecting EMI according to one example. At block 102, a cardiac event is sensed by the sensing circuit 86. In the illustrative examples presented herein, the cardiac event is an R-wave sensed in response to a cardiac electrical signal received by sensing circuit 86 crossing an R-wave sensing threshold. The R-wave sensing threshold may be an auto-adjusted sensing threshold, which may include one or more decay rates and/or step changes between a starting threshold amplitude and a minimum threshold amplitude or sensing floor (also referred to as "sensitivity"). For example, the R-wave sensing threshold may be a multi-level sensing threshold as generally disclosed in the above-incorporated pending U.S. patent application Ser. No. 15/142,171 (Cao, et al). It is contemplated, however, that the process of flow chart 100 for detecting EMI may be performed during P-wave sensing, in which case the sensed cardiac event at block 102 is a P-wave.

In response to the sensed cardiac event, control circuit 80 stores a segment of a cardiac electrical signal segment at block 104. In one example, the cardiac event sensed at block 102 is sensed from a first cardiac electrical signal by R-wave detector 66 of first sensing channel 83. The control circuit 80 receives the R-wave sensed event signal and in response triggers the storage of a segment of a second cardiac electrical signal received by second sensing channel 85. In other examples, the stored cardiac signal segment may be a segment of the same cardiac electrical signal from which the cardiac event was sensed.

The stored cardiac signal segment may be a predetermined number of sample points or time interval and may extend before and after the sensed cardiac event. For instance, the segment may include 92 sample points acquired at a 256 Hz sampling rate, or approximately 360 ms long. Of the 92 sample points, 68 sample points may precede and include the sample point at which the R-wave sensed event signal was received and 24 sample points may extend after the sample point at which the R-wave sensed event signal was received. Other sampling rates and sampling segment time lengths (or total number of sample points) may be used, however it is desirable to include a portion of the cardiac electrical signal extending before and/or after a QRS complex that would correspond to a potentially valid R-wave sensed event signal so that EMI occurring during a baseline portion of the signal may be detected. In the illustrative embodiments described herein, more sample points are obtained earlier than the R-wave sensed event signal and fewer are obtained after the R-wave sensed event signal. This allows detection of EMI prior to the R-wave sensed event signal and early processing results of the cardiac signal segment. In other examples, the segment may be centered or off-centered relative to the time of the R-wave sensed event signal and the sensed cardiac event may occur relatively earlier or later in the stored cardiac signal segment.

At block 106, the cardiac signal segment is notch filtered. Control circuit 80 may establish a noise threshold for applying to the cardiac signal segment by obtaining the notch filtered signal segment. The notch filtered signal segment may be acquired and stored simultaneously with the cardiac electrical signal segment. Simultaneous determination and storage of the notch filtered signal segment with the cardiac electrical signal segment may be performed when the analysis of the cardiac signal segment for detecting EMI is performed on an event-by-event basis. Alternatively, the notch filtered segment is obtained as needed when analysis of the cardiac signal segment is being performed for detecting EMI. As described above, the notch filter may be a digital filter implemented in firmware as part of the signal processing performed by second sensing channel 85 under the control of control circuit 80. Alternatively, the notch filter is a hardware implemented filter included in sensing circuit 86.

The cardiac signal segment is compared to the notch filtered signal segment at block 108 to identify and count the number of times the stored cardiac signal segment crosses the notch filtered signal segment. One method for counting noise threshold crossings is described below in conjunction with FIG. 9.

The value of the noise threshold crossing count is compared to EMI event criteria at block 112. For example, control circuit 80 may be configured to detect EMI occurring at or above a selected frequency by setting a count threshold based on the number of crossings expected to occur if EMI at the selected frequency were present for the entire cardiac electrical signal segment. If control circuit 80 is configured to detect EMI occurring at 20 Hz and higher, fourteen threshold crossings are expected to occur during the 92 sample point segment of the cardiac electrical signal sampled at 256 Hz. If control circuit 80 is configured to detect EMI at 50 Hz or higher, 36 threshold crossings are expected. The threshold count value may be programmable or the minimum EMI frequency to be detected may be programmable. Using a programmed minimum EMI frequency to be detected, control circuit 80 may be configured to compute the threshold count value based on the following equation:

$$\text{Threshold} = (\text{EMI freq}/\text{SampFreq}) * \text{NSampPts} * 2$$

where EMI freq is the selected minimum frequency to be detected, SampFreq is the sampling rate used to store the cardiac signal segment, and NSampPts is the total number of sample points included in the segment. The total number of sample points is multiplied by the ratio of the selected EMI frequency to the sampling frequency used to obtain the cardiac signal segment to give the number of EMI cycles expected during the signal segment. This number is doubled to obtain the threshold count value when both positive and negative threshold crossings are counted. If only positive-going (or only negative-going) crossings are counted, the multiple of two may be omitted from the above equation.

If the value of the noise threshold crossing count equals or exceeds the EMI event threshold at block 112, control circuit 80 detects EMI in the cardiac electrical signal segment and may identify the sensed cardiac event that triggered the cardiac signal segment storage as an EMI event at block 114. If the value of the noise threshold crossing count does not reach the EMI event threshold, EMI is not detected (block 110). Control circuit 80 waits for the next sensed cardiac event at block 102. In some examples, control circuit 80 may be configured to determine the frequency of the EMI that was detected during the cardiac electrical signal segment at block 116. The EMI frequency may be computed using the EMI frequency equation above and described in conjunction with FIG. 7. The EMI frequency may be stored in memory 82 for transmission to external device 40 to inform the clinician of EMI exposure of the patient.

An EMI index may be updated at block 118. For example, the EMI index may be the number of identified EMI events out of a total number of sensed cardiac events over a predetermined time interval and/or cumulatively since the time of ICD implantation and/or since the last telemetry interrogation of ICD 14 by external device 40. One or more EMI indices, e.g., corresponding to different time intervals (24 hours, one week, etc.), may be stored in memory 82. The detected EMI frequency(ies) may be stored with the EMI indices. If more than one frequency is detected, separate EMI indices may be determined for different detected frequencies. For example, separate counts or percentages of EMI events out of all sensed events may be stored for different frequency ranges such as 20±10 Hz, 40±10 Hz and/or 60±10 Hz.

In some examples, control circuit 80 may determine if EMI alert criteria are met at block 120 based on the EMI index. The EMI index may be compared to an alert threshold, e.g., if more than 20% of sensed events are identified as EMI events, control circuit 80 may generate an alert. The alert may be a patient alert generated by patient alert circuit 94, such as a vibration or audible tone, which is perceivable by the patient. The patient may be prospectively instructed to move away from an EMI environment upon perceiving the patient alert. Additionally or alternatively, control circuit 80 may control telemetry circuit 88 to transmit an EMI alert signal in response to an EMI index that meets EMI alert criteria. The alert signal may be transmitted via telemetry circuit 88 to an external device, e.g., external device 40 (FIG. 1A), to alert a clinician to the EMI exposure of the patient.

At block 122, control circuit 80 may determine if RRI-based tachyarrhythmia detection criteria are met according to an implemented tachyarrhythmia detection algorithm. In some examples, tachyarrhythmia detector 92 includes VT and VF interval counters that count the number of RRIs that fall within a respective VT interval zone and VF interval zone. Tachyarrhythmia detector 92 may be configured to detect tachyarrhythmia when a VT or VF counter reaches a required number of intervals to detect (NID) and EMI is not being detected. As such, if tachyarrhythmia detector 92 is detecting tachyarrhythmia, control circuit 80 determines if EMI detection criteria are met at block 124.

EMI may be detected in response to an EMI event count that reaches or exceeds a threshold value, for example when two out of the most recent eight sensed R-waves are identified as EMI events. If tachyarrhythmia detection criteria based on RRIs (and/or other tachyarrhythmia detection criteria) are satisfied at block 122, but EMI is being detected at block 124, control circuit 80 withholds the tachyarrhythmia detection at block 126. The EMI event count used for detecting EMI for withholding a tachyarrhythmia detection may be different than the EMI index determined at block 118 for generating a patient and/or clinician alert. For instance an EMI index may be determined over a relatively longer period of time, such as a predetermined number of minutes, hours, one day or one week, while the EMI event count used to withhold tachyarrhythmia detection may be determined over the most recent Y sensed cardiac events, e.g., eight to twelve cardiac events, and is generally within the number of cardiac cycles required to detect the tachyarrhythmia.

If tachyarrhythmia detection and therapy are withheld at block 126, the process returns to block 102 to continue sensing cardiac events and may detect tachyarrhythmia at a later time if tachyarrhythmia detection criteria are met, or are still being met, and EMI is not being detected at block 124. If tachyarrhythmia is being detected by tachyarrhythmia detector 92 and control circuit 80 is not detecting EMI at block 124, control circuit 80 confirms the tachyarrhythmia detection at block 128 and controls therapy delivery circuit 84 to deliver therapy, e.g., ATP and/or a high energy shock pulse according to a programmed tachyarrhythmia therapy protocol.

Figure 9:
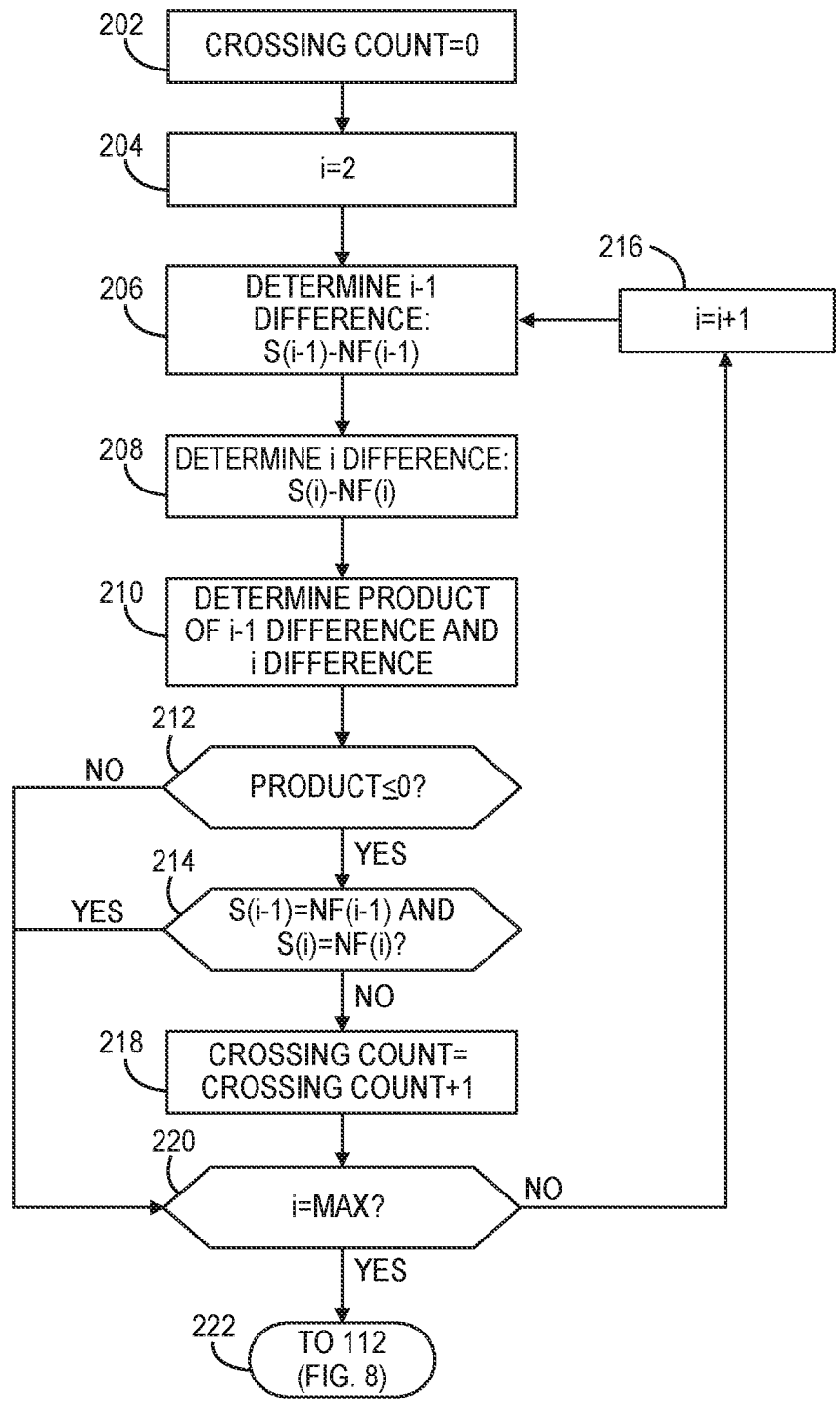
FIG. 9 is a flow chart of one method that may be performed at block 108 of FIG. 8 for counting noise threshold crossings.

FIG. 9 is a flow chart of one method that may be performed at block 108 of FIG. 8 for counting noise threshold crossings by control circuit 80 for determining a noise threshold crossing count. At block 202, a noise threshold crossing counter is initialized to a value of zero. A sample number "i" is initialized to 2 at block 204. The stored cardiac signal segment and the notch filtered signal segment may each have sample points 1 through 92, as in the example given above.

At block 206, the difference between the i−1 cardiac signal segment sample point, S(i−1), and the i−1 notch filtered signal segment sample point, NF(i−1), is determined. At block 208, the difference between the ith cardiac signal sample point, S(i), and the ith notch filtered signal segment sample point, NF(i), is determined. The product of these two differences is compared to zero at block 210. If the cardiac signal segment crosses the noise threshold at the ith sample point, one difference determined at block 206 or 208 is negative and the other difference is positive. The resulting product at block 210 will be negative.

If the cardiac signal segment is above the notch-filtered signal or below the notch-filtered signal, both sample points S(i−1) and S(i) are greater than or both are less than the respective NF(i−1) and NF(i) sample points. The product at block 210 will be positive. If the product is greater than zero, "no" branch of block 212, the ith sample point of the cardiac signal segment is not a noise threshold crossing and is not counted. If the last sample point of the cardiac signal segment has not been reached (e.g., the sample point number i has not reached 92), as determined at block 220, the process advances to block 216 to increase the value of i by 1 to compare the next sample point of the cardiac signal segment to the next corresponding sample point of the notch filtered signal segment.

If the product of the determined differences is zero at block 212, one or both of the differences determined at blocks 206 and 208 are zero, indicating approximately equal values of the respective cardiac signal sample point and the notch filtered signal sample point, which may or may not be a noise threshold crossing. Additional criteria are applied at block 214 to determine if the ith sample point should be counted as a noise threshold crossing.

At block 214, the values of the paired S(i−1) and NF(i−1) sample points are compared to each other and the values of the paired S(i) and NF(i) are compared to each other. If both paired sample points are approximately equal to each other, i.e., if S(i−1) equals NF(i−1) and S(i) equals NF(i)), the two cardiac signal segment sample points S(i−1) and S(i) may represent a baseline or flatline portion of the cardiac signal segment. In this case, the ith sample point is not counted as a noise threshold crossing. The process advances to the next sample point by returning to block 216 if the last sample point has not yet been reached ("no" branch of block 220).

If at least one of the paired cardiac signal segment and notch filtered signal sample points, the i−1 or ith paired sample points, are not approximately equal to each other ("no" branch of block 214), the two consecutive points S(i) and S(i−1) of the cardiac signal segment are not a baseline or flatline portion of the signal segment and may be a noise threshold crossing if the product at block 212 is less than or equal to zero.

Determination of equality at block 214 may allow for the paired sample points to be within a predetermined range of each other to be considered equal, e.g., within 10%, 15% or other percentage or predetermined value of each other. In one example, the test for equality of the paired sample points at block 214 may include comparing the first difference to an equality threshold by comparing the i−1 difference determined at block 206 to an equality threshold or range and comparing the second difference, the ith difference determined at block 208, to the equality threshold or range. If the absolute values of both differences are less than or equal to the equality threshold or within the equality range, both paired sample points are found to be equal at block 214. The process follows the "yes" branch of block 214, and the noise threshold crossing count is not increased. If at least one difference is greater than the equality threshold or outside the equality range, the "AND" operation of block 214 is false. The criteria for detecting a noise threshold crossing is satisfied ("no" branch of block 214).

A noise threshold crossing is detected based on the product comparison of block 212 and the criteria of block 214. Control circuit 80 increases the crossing count by one at block 218. If the last sample point has not been reached ("no" branch of block 220), the process advances to the next sample point by returning to block 216 and continues counting noise threshold crossings. After reaching the last sample point ("yes" branch of block 220), the control circuit 80 advances to block 112 of FIG. 8 as indicated at block 222.

Figure 10:
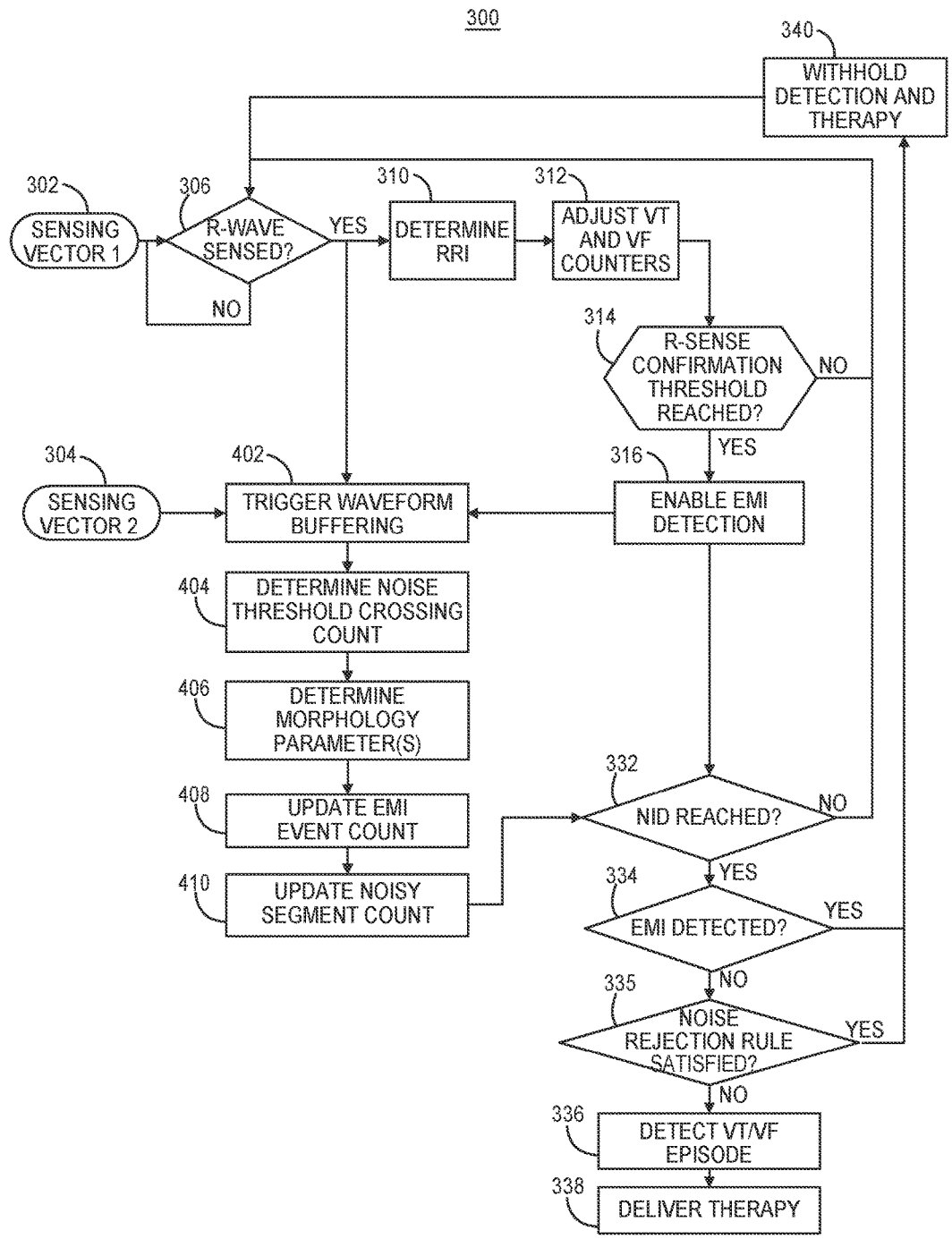
FIG. 10 is a flow chart of a method performed by an ICD for detecting EMI and withholding tachyarrhythmia detection in response to EMI detection.

FIG. 10 is a flow chart 300 of a method performed by ICD 14 for detecting EMI and withholding tachyarrhythmia detection in response to EMI detection according to one example. At blocks 302 and 304, two different sensing electrode vectors are selected by sensing circuit 86 for receiving a first cardiac electrical signal by first sensing channel 83 and a second cardiac electrical signal by second sensing channel 85. Sensing circuit 86 may produce an R-wave sensed event signal at block 306 in response to the first sensing channel 83 detecting an R-wave sensing threshold crossing by the first cardiac electrical signal. The R-wave sensed event signal may be passed to timing circuit 90 for determining an RRI (block 310) ending with the current R-wave sensed event signal and beginning with the most recent preceding R-wave sensed event signal.

The timing circuit 90 of control circuit 80 may pass the RRI timing information to the tachyarrhythmia detection circuit 92 which adjusts tachyarrhythmia interval counters at block 312. If the RRI is shorter than a tachycardia detection interval (TDI) but longer than a fibrillation detection interval (FDI), i.e., if the RRI is in a tachycardia detection interval zone, a VT interval counter is increased at block 312. If the VT interval counter is configured to count consecutive VT intervals for detecting VT, the VT interval counter may be reset to zero if the RRI is longer than the TDI. If the RRI is shorter than the FDI, the VF counter is increased. The VF counter may be a probabilistic VF counter that counts VF intervals in an X of Y interval such that VF may be detected when a threshold number of VF intervals are detected which are not required to be consecutive. In some examples, a combined VT/VF interval counter is increased if the RRI is less than the TDI.

After updating the tachyarrhythmia interval counters at block 312, tachyarrhythmia detector 92 compares the VT and VF interval counter values to an R-sense confirmation threshold at block 314. If a VT or VF detection interval counter has reached an R-sense confirmation threshold, "yes" branch of block 314, control circuit 80 enables EMI detection at block 316. In the example of FIG. 8, EMI detection may be performed on an event-by-event basis. In the example of FIG. 10, identification of an R-wave sensed event signal as an EMI event may be performed only after a VT or VF interval counter has reached an R-sense confirmation threshold. Additionally or alternatively to applying an R-sense confirmation threshold to the individual VT and VF counters, an R-sense confirmation threshold may be applied to a combined VT/VF interval counter. The R-sense confirmation threshold may be a value of one or more. Different R-sense confirmation thresholds may be applied to the VT interval counter and the VF interval counter. For example, the R-sense confirmation threshold may be a count of two on the VT interval counter and a count of three on the VF interval counter. In other examples, the R-sense confirmation threshold is a higher number, for example five or higher, but may be less than the number of VT or VF intervals required to detect VT or VF, respectively.

If the R-sense confirmation threshold is not reached by any of the tachyarrhythmia interval counters at block 314, the control circuit 80 returns to block 306 and waits for the next R-wave sensed event signal. If the R-sense confirmation threshold is reached at block 314, the control circuit 80 enables EMI detection at block 316. EMI detection is enabled by enabling buffering of cardiac signal segments at block 402 in response to each R-wave sensed event signal from first sensing channel 83. A cardiac signal segment from the second cardiac electrical signal may be buffered in memory 82 at block 402.

A digitized segment of the second cardiac electrical signal may be sampled over a time segment defined relative to the sample point time of the R-wave sensing threshold crossing and corresponding R-wave sensed event signal received from sensing circuit 86. The digitized segment may be 100 to 500 ms long, for instance. In one example, the buffered segment of the second cardiac electrical signal is at least 92 sample points obtained at a sampling rate of 256 Hz, or approximately 360 ms, of which 68 sample points may precede and include the sample point at which the R-wave sensed event signal was received and 24 sample points may extend after the sample point at which the R-wave sensed event signal was received.

The buffered cardiac signal segment is used for determining if the sensed R-wave that triggered buffering of the cardiac signal segment is an EMI event using the techniques disclosed herein. In other examples, the cardiac signal segment buffered at block 402 may be acquired from the first cardiac electrical signal from first sensing channel 83. In still other examples, a cardiac signal segment from the first cardiac electrical signal and from the second cardiac electrical signal corresponding to each R-wave sensed event signal may be stored in memory 82 and analyzed for determining if the sensed R-wave is an EMI event.

Control circuit 80 determines a count of noise threshold crossings in the buffered cardiac signal segment at block 404. Control circuit 80 establishes the noise threshold by applying a notch filter to the stored cardiac signal segment as described above in conjunction with FIG. 7. The notch filter may correspond to the filter described in conjunction with FIG. 6, which significantly attenuates 50-60 Hz electrical noise, muscle noise, other EMI, and other noise/artifacts in the cardiac electrical signal segment.

The noise threshold crossing count is determined by comparing sample points of the cardiac signal segment to the notch filtered signal segment. The value of the noise threshold crossing count may be compared to a count threshold at block 408 for updating an EMI event count. If the number of noise threshold crossings during the cardiac signal segment is equal to or greater than the count threshold, the R-wave sensed event that triggered the storage of the cardiac signal segment may be identified as an EMI event at block 408, and the EMI event count is increased.

In some examples, control circuit 80 may additionally determine one or more morphology parameters from the cardiac signal segment at block 406 before updating the EMI event count at block 408. A combination of one or more morphology parameters and the noise threshold crossing count may be compared to EMI event criteria at block 408. Morphology parameters may include, but are not limited to, a low slope content, a noise pulse count, a normalized rectified amplitude, a maximum signal width, or other noise metrics. Examples of morphology parameters that may be determined are generally disclosed in the above-incorporated U.S. Pat. No. 7,761,150 (Ghanem, et al.) and U.S. Pat. No. 8,437,842 (Zhang, et al). The morphology parameters may be determined using the entire second cardiac signal segment stored at block 404 or a portion of the stored segment. In one example, at least 92 sample points, approximately 360 ms, are analyzed for determining the noise threshold crossing count at block 404 and morphology parameters at block 406, which may be a portion of or the entire stored cardiac signal segment.

The portion of the signal segment analyzed for determining morphology parameters at block 406 may extend beyond an expected QRS signal width so that at least a portion of the cardiac signal segment being analyzed corresponds to an expected baseline portion. In this way, a morphology parameter, such as a noise pulse count, may be determined which is correlated to non-cardiac signal noise that may be occurring during the baseline portion of the cardiac signal segment. Morphology parameters determined at block 406, therefore, may be "gross" morphology parameters that represent the morphology of the cardiac signal segment as a whole and are not necessarily limited to the morphology of the event or waveform sensed as an R-wave.

In one example, control circuit 80 determines three morphology parameters at block 406. The three morphology parameters may include a baseline noise parameter, an amplitude parameter, and a signal width parameter as generally disclosed in the above-incorporated provisional U.S. Pat. Application No. 62/367,166. The baseline noise parameter may be determined as a count of signal pulses during the second cardiac electrical signal segment. In one example, a first order differential signal is determined from the notch-filtered second cardiac electrical signal segment. The first order differential signal may be computed by computing successive differences, $A(n)-A(n-1)$, between sample points, where n is the sample point number, ranging from 1 to 92 in the example given above, $A(n)$ is the amplitude of the nth sample point and $A(n-1)$ is the amplitude of the immediately preceding $n-1$ sample point.

Zero crossings of the first order differential signal are set by identifying consecutive sample points of the differential signal having opposite polarity. For example a positive sample point followed by a negative sample point is identified as a zero crossing, and a negative sample point followed by a positive sample point is identified as a zero crossing. Control circuit 80 compares the absolute values of the two signal sample points identified as a zero crossing. The sample point of the differential signal having the smaller absolute value amplitude is set to zero amplitude to clearly demark each zero crossing with two consecutive zero crossings defining a baseline noise pulse.

The differential signal with zero crossings set may be rectified and a noise pulse amplitude threshold may be determined from the rectified differential signal. For example, the noise pulse amplitude threshold may be determined based on the maximum amplitude of the rectified differential signal over the entire segment being analyzed, e.g., over 360 ms in the example given above. The noise pulse amplitude threshold may be set to a portion or percentage of the maximum amplitude. For instance, the noise pulse amplitude threshold may be set to be one-eighth of the maximum amplitude of the rectified differential signal in one example.

Signal pulses within the rectified, differential signal segment are identified and counted. If the sample point amplitude between two consecutive zero crossings crosses the noise pulse amplitude threshold, a signal pulse is counted. In some examples, a signal pulse is counted only if the pulse width is less than a certain threshold (e.g., 6 sample points or less) and the pulse crosses the noise pulse amplitude threshold. The control circuit 80 counts all pulses exceeding the noise pulse amplitude threshold in the segment. The signal pulse count value may be determined as the baseline noise parameter at block 406. Other techniques that may be implemented for determining a baseline noise parameter at block 406 are generally disclosed in U.S. Pat. No. 8,435,185 (Ghanem, et al.), incorporated herein by reference in its entirety.

The amplitude parameter may also be determined at block 406 from the notch-filtered second cardiac electrical signal segment. Control circuit 80 may be configured to determine the maximum absolute amplitude of the rectified, notch-filtered cardiac signal segment. The amplitudes of all sample points of the notch-filtered, rectified signal segment may be summed and normalized by the maximum absolute amplitude. The normalized rectified amplitude (NRA) may be determined as four times the summed amplitudes divided by the maximum absolute amplitude. The higher this NRA, the more likely the second cardiac signal segment contains a large signal that is a valid R-wave of a VT or VF episode. The sensed R-wave may be identified as a potential shockable event that should be used in counting tachyarrhythmia detection intervals when the amplitude parameter is greater than a shockable amplitude threshold. If the sensed R-wave is classified is a potential shockable event based on the amplitude parameter, this classification may overrule an EMI event classification in some examples.

A signal width parameter may be determined at block 406 using the notch-filtered, rectified signal segment that is also used for determining the signal amplitude parameter. In order to determine the signal width parameter, control circuit 80 may first identify signal pulses in the signal segment having a peak amplitude that is greater than or equal to a pulse amplitude threshold. A maximum signal width may then be determined from among these identified signal pulses.

The pulse amplitude threshold used to identify these signal pulses may be based on the maximum absolute amplitude of the notch-filtered, rectified signal segment. This pulse amplitude threshold may be a different threshold than the noise pulse amplitude threshold used for counting signal pulses for obtaining a baseline noise parameter. For example, the pulse amplitude threshold used for determining the signal width parameter may be set to half the maximum absolute amplitude of the rectified, notch-filtered signal segment whereas the noise pulse amplitude threshold used to determine a count of signal pulses may be set to one-eighth the maximum amplitude of the rectified, differential signal segment.

The maximum signal width may be determined only from signals reaching a peak amplitude criterion. For example, the maximum peak of each signal pulse is determined, and all pulses having a maximum peak that is greater than or equal to the pulse amplitude threshold, e.g., greater than half the maximum absolute amplitude, are identified. Of these identified signal pulses, the signal pulse having the greatest pulse width is identified. Control circuit 80 may determine the signal width for the identified pulses as the number of sample points (or corresponding time interval) between a pair of consecutive zero crossings of the rectified, notch-filtered signal. This greatest pulse width is determined as the maximum pulse width of the second cardiac electrical signal segment. A large signal width may be evidence of an R-wave that is valid for use in detecting VT or VF. A large signal width, therefore, may indicate a potentially shockable event and preclude identification of the sensed R-wave as being an EMI event At block 408, control circuit 80 may determine if the sensed R-wave is identified as an EMI event based on the noise threshold crossing count determined at block 404 and the morphology parameters determined at block 406. Control circuit 80 fetches the signal amplitude and the signal width morphology parameters and the noise threshold crossing count for comparison to EMI event criteria. If the signal amplitude parameter and/or signal width parameter are greater than respective thresholds, the sensed R-wave is not identified as an EMI event. The large signal amplitude and/or signal width indicate a valid sensed R-wave and therefore potentially a shockable beat. In the example given above, NRA may be compared to a potential shockable beat amplitude threshold. When the NRA is determined as described above, the potential shockable beat amplitude threshold may be set between 100 and 150, and to 140 in some examples. If the NRA is greater than the threshold, the signal segment is likely to include a true R-wave and is therefore a potential shockable beat (if it is occurring at a VT or VF interval).

The pulse width parameter may be compared to a potential shockable beat width threshold. In one example, the potential shockable beat width threshold is set to 20 sample points when the sampling rate is 256 Hz. If the NRA and the maximum pulse width for the signal segment are both greater than the respective amplitude and width thresholds, the sensed R-wave is not identified as an EMI event, regardless of the noise threshold crossing count. In other examples, only one of the amplitude parameter or the signal width parameter may be required to exceed its respective threshold in order to identify the sensed R-wave as a potentially shockable beat, and not as an EMI event regardless of the noise threshold crossing count.

If the cardiac signal segment is not identified as a potential shockable beat, the noise threshold crossing count may be compared to a count threshold value at block 410. If the noise threshold count value is greater than or equal to the count threshold, the sensed R-wave is identified as an EMI event. Control circuit 80 updates an EMI event count at block 408. A count of sensed R-waves identified as EMI events based on the noise threshold crossing count exceeding a count threshold when the cardiac signal segment is not identified as a potential shockable beat is updated. An X of Y counter may be updated for counting the number of EMI events out of a predetermined number (Y) of the most recent consecutively sensed R-waves. For example the EMI event count may count the number of EMI events identified out of the most recent eight consecutively sensed R-waves. In other examples, a counter may be configured to count the number of consecutively sensed R-waves that are identified as EMI events and be reset to zero at block 408 if the sensed R-wave is not identified as an EMI event.

Control circuit 80 may be configured to update a noisy segment count at block 410 based on the morphology parameters determined at block 406. In some examples, the cardiac signal segment may be identified as a noisy segment based on the baseline noise parameter whether or not the sensed event is not identified as an EMI event at block 408 based on the noise threshold crossing count.

The baseline noise parameter determined as the signal pulse count may be compared to a first noise threshold if the segment is identified as a potential shockable beat based on the signal amplitude and/or signal width parameters. For example, if the signal pulse count determined as the baseline noise parameter is greater than the first noise threshold, e.g., greater than 12, the cardiac electrical signal segment is identified as a noisy segment at block 410. If the signal pulse count is less than the first noise threshold, the cardiac signal segment is not identified as a noisy segment.

If the cardiac signal segment is not identified as a potential shockable beat based on the signal amplitude and/or signal width parameters, the baseline noise parameter may be compared to a second noise threshold at block 410. The second noise threshold may be lower than the first noise threshold. If the segment is not identified as a potential shockable beat, less stringent criteria, e.g., a lower noise threshold, may be applied for classifying the segment as a noisy segment. In one example, the second noise threshold is six when the baseline noise parameter is determined as the signal pulse count as described above. If the baseline noise parameter meets or exceeds the second noise threshold when the cardiac signal segment is not identified as a potential shockable beat, the cardiac signal segment is identified as a noisy segment at block 410. Control circuit 80 updates the noisy segment count at block 410 to track the number of noisy segments that are identified out of a predetermined number of most recent cardiac signal segments, e.g., out of the most recent eight cardiac signal segments.

If the NID is reached by a VT or VF interval counter at block 332, the value of the EMI event count is compared to an EMI detection threshold at block 334. For example if two out of the most recent eight sensed events are counted as EMI events, EMI is detected at block 334. The VT or VF detection based on the NID being reached is withheld at block 340, and no therapy is delivered. In order to detect VT or VF, the NID is required to be reached when EMI detection criteria are not satisfied at block 334.

If EMI is not detected at block 334, control circuit 80 may determine if a noise rejection rule is satisfied at block 335 based on the updated noisy segment count. The noise rejection rule may be satisfied at block 335 if the noisy segment count reaches a threshold number of noisy segments. For example, if at least two out of the most recent eight (or other predetermined number) analyzed cardiac electrical signal segments are identified as noisy segments, the noise rejection rule is satisfied at block 335. VT or VF detection based on the NID being reached at block 332 is withheld at block 340, and no therapy is delivered. If less than two out of the most recent eight analyzed cardiac electrical signal segments are classified as noisy, the rejection rule is not satisfied.

If EMI is not detected at block 334 and the noise rejection rule is not satisfied at block 335, control circuit 80 detects VT or VF at block 336 based on the respective VT or VF NID being reached. Control circuit 80 controls therapy delivery circuit 84 to deliver therapy at block 338, e.g., ATP and/or cardioversion/defibrillation shock(s), according to a programmed therapy protocol.

In some examples, other VT/VF detection rejection rules may be applied at block 335 based on analysis of the cardiac electrical signal segments buffered at block 402. The methods for detecting EMI and withholding VT/VF detection and therapy as disclosed herein may be combined with additional analyses of the stored cardiac signal segments disclosed in the above-incorporated provisional U.S. Patent Application Nos. 62/367,166, 62/367,221 and 62/367,170 and U.S. patent application Ser. No. 15/140,802 (Zhang, et al.). Additional analyses may be performed for determining morphology parameters, comparing the parameters to various rejection rules, such as an R-wave morphology rejection rule, a T-wave oversensing rejection rule and/or other noise rejection rules. When a rejection rule is satisfied, the VT or VF detection based on the NID being reached may be withheld.

Thus, a method and apparatus for detecting EMI in a cardiac electrical signal and withholding a ventricular tachyarrhythmia detection and therapy in response to detecting EMI by an extra-cardiovascular ICD system have been presented in the foregoing description with reference to specific embodiments. In other examples, various methods described herein may include steps performed in a different order or different combination than the illustrative examples shown and described herein. It is appreciated that various modifications to the referenced embodiments may be made without departing from the scope of the disclosure and the following claims.

The invention claimed is:

1. An extra-cardiovascular implantable cardioverter defibrillator (ICD) comprising:
a therapy delivery circuit configured to deliver a tachyarrhythmia therapy to a patient's heart via extra-cardiovascular electrodes;
a sensing circuit configured to receive a first cardiac electrical signal via a first extra-cardiovascular sensing electrode vector and sense a cardiac event in response to the first cardiac electrical signal crossing a sensing threshold amplitude;
a memory; and
a control circuit coupled to the sensing circuit, the therapy delivery circuit and the memory, the control circuit configured to:
store a cardiac signal segment in the memory in response to the sensing circuit sensing the cardiac event;
obtain a notch filtered signal segment by notch filtering the cardiac signal segment;
determine a count of crossings of the notch filtered signal segment by the cardiac signal segment;
determine whether electromagnetic interference (EMI) is present in the cardiac signal segment based on a value of the count; and
withhold a tachyarrhythmia therapy in response to determining that EMI is present.

2. The ICD of claim 1, wherein the control circuit is configured to store the cardiac signal segment from the first cardiac electrical signal.

3. The ICD of claim 1, wherein:
the sensing circuit is further configured to receive a second cardiac electrical signal via a second extra-cardiovascular sensing electrode vector different than the first extra-cardiovascular sensing electrode vector; and
the control circuit is configured to store the cardiac signal segment from the second cardiac electrical signal.

4. The ICD of claim 1, wherein the control circuit is configured to store the cardiac signal segment by:
storing a first number of sample points of the cardiac signal segment that occur earlier than the sensed cardiac event; and
store a second number of sample points of the cardiac signal segment that occur later than the sensed cardiac event, the first number greater than the second number.

5. The ICD of claim 1, wherein the control circuit is configured to determine the count of the crossings of the notch filtered signal segment by:
determining a first difference between a first cardiac signal segment sample point and a corresponding first notch filtered signal sample point;
determining a second difference between a second cardiac signal segment sample point and a corresponding second notch filtered signal sample point;
determining a product of the first difference and the second difference; and
increasing the count of the crossings of the notch filtered signal segment in response to the product being negative.

6. The ICD of claim 5, wherein the control circuit is further configured to determine the count of the crossings of the notch filtered signal segment by:
comparing the first difference to an equality threshold;
comparing the second difference to an equality threshold; and
increasing the count of the crossings of the notch filtered signal segment in response to the at least one of the first difference and the second difference being greater than the equality threshold.

7. The ICD of claim 1, wherein the control circuit is configured to determine the count of the crossings of the notch filtered signal segment by:
determining a first difference between a first cardiac signal segment sample point and a corresponding first notch filtered signal sample point;
determining a second difference between a second cardiac signal segment sample point and a corresponding second notch filtered signal sample point;
determining a product of the first difference and the second difference;
in response to the product being zero, comparing the first difference to an equality threshold and comparing the second difference to the equality threshold; and
increasing the count of the crossings of the notch filtered signal segment in response to the at least one of the first difference and the second difference being greater than the equality threshold.

8. The ICD of claim 1, wherein the control circuit is configured to determine whether EMI is present in the cardiac signal segment by:
setting a threshold count value based on a ratio of an EMI frequency to be detected and a sampling rate of the cardiac signal segment;
comparing the value of the count to the threshold count value; and
detecting EMI in the cardiac signal segment in response to the value of the count being equal to or greater than the threshold count value.

9. The ICD of claim 1, wherein the control circuit is further configured to determine a frequency of the EMI based on the count of the crossings of the notch filtered signal segment in response to determining EMI is present in the cardiac signal segment.

10. The extra-cardiovascular ICD of claim 1, wherein:
the sensing circuit is further configured to receive a second cardiac electrical signal via a second extra-cardiovascular sensing electrode vector different that the first extra-cardiovascular sensing electrode vector;
the control circuit is further configured to:
determine a morphology parameter from the second cardiac electrical signal in response to a cardiac event sensed by the sensing circuit from the first cardiac electrical signal;
compare the morphology parameter to potential shockable beat criteria; and
determine that EMI is not present in the cardiac signal segment in response to the potential shockable beat criteria being satisfied.

11. The ICD of claim 1, wherein the control circuit is further configured to:
determine an EMI index in response to determining that EMI is present in the cardiac signal segment;
compare the EMI index to alert criteria; and
generate an alert in response to the EMI index satisfying the alert criteria.

12. The ICD of claim 1, wherein the control circuit is further configured to:
determine event intervals between consecutive cardiac events sensed by the sensing circuit;
compare the event intervals to a tachyarrhythmia detection interval;

increase a tachyarrhythmia interval count in response to each of one of the determined event intervals that is less than the tachyarrhythmia detection interval; and determine the count of the crossings of the notch filtered signal segment by the cardiac signal segment in response to the tachyarrhythmia interval count being greater than a sensed event confirmation threshold.

13. The ICD of claim 1, wherein the control circuit is further configured to:

update an EMI event count in response to determining EMI is present in the cardiac signal segment;

determine event intervals between consecutive cardiac events sensed by the sensing circuit;

compare the event intervals to a tachyarrhythmia detection interval;

increase a tachyarrhythmia detection interval count in response to each one of the determined event intervals that is less than the tachyarrhythmia detection interval;

compare the tachyarrhythmia detection interval count to a tachyarrhythmia detection threshold;

compare the EMI event count to EMI detection criteria in response the tachyarrhythmia detection interval count being equal to or greater than the tachyarrhythmia detection threshold; and withhold detection of a tachyarrhythmia in response to the EMI event count satisfying the EMI detection criteria.

14. The extra-cardiovascular ICD of claim 1, wherein the control circuit is further configured to:

detect a tachyarrhythmia from the first cardiac electrical signal; and deliver the tachyarrhythmia therapy in response to detecting the tachyarrhythmia and determining that EMI is not present in the cardiac signal segment.

15. The extra-cardiovascular ICD of claim 1, further comprising a housing enclosing the therapy delivery circuit, the sensing circuit, the memory and the control circuit and having a connector block for receiving an extra-cardiovascular lead carrying at least one electrode of the first extra-cardiovascular sensing electrode vector.

16. A method performed by an extra-cardiovascular implantable cardioverter defibrillator (ICD) comprising:

receiving a first cardiac electrical signal via a first extra-cardiovascular sensing electrode vector by a sensing circuit of the ICD;

sensing a cardiac event by the sensing circuit in response to the first cardiac electrical signal crossing a sensing threshold amplitude;

storing a cardiac signal segment in memory of the ICD in response to the sensing circuit sensing the cardiac event;

obtaining a notch filtered signal segment by notch filtering the cardiac signal segment;

determining a count of crossings of the notch filtered signal segment by the cardiac signal segment;

determining whether electromagnetic interference (EMI) is present in the cardiac signal segment based on a value of the count; and withholding a tachyarrhythmia therapy in response to determining that EMI is present.

17. The method of claim 16, wherein storing the cardiac signal segment comprises storing the cardiac signal segment from the first cardiac electrical signal.

18. The method claim 16, further comprising receiving a second cardiac electrical signal by the sensing circuit via a second extra-cardiovascular sensing electrode vector different than the first extra-cardiovascular sensing electrode vector, wherein storing the cardiac signal segment comprises storing the cardiac signal segment from the second cardiac electrical signal.

19. The method of claim 16, wherein storing the cardiac signal segment comprises:

storing a first number of sample points of the cardiac signal segment that occur earlier than the sensed cardiac event; and storing a second number of sample points of the cardiac signal segment later than the sensed cardiac event, the first number greater than the second number.

20. The method 16, wherein determining the count of the crossings of the notch filtered signal segment comprises:

determining a first difference between a first cardiac signal segment sample point and a corresponding first notch filtered signal sample point;

determining a second difference between a second cardiac signal segment sample point and a corresponding second notch filtered signal sample point;

determining a product of the first difference and the second difference; and increasing the count of the crossings of the notch filtered signal segment in response to the product being negative.

21. The method of claim 20, wherein determining the count of the crossings of the notch filtered signal segment comprises:

comparing the first difference to an equality threshold;

comparing the second difference to an equality threshold; and increasing the count of the crossings of the notch filtered signal segment in response to the at least one of the first difference and the second difference being greater than the equality threshold.

22. The method of claim 16, wherein determining the count of the crossings of the notch filtered signal segment comprises:

determining a first difference between a first cardiac signal segment sample point and a corresponding first notch filtered signal sample point;

determining a second difference between a second cardiac signal segment sample point and a corresponding second notch filtered signal sample point;

determining a product of the first difference and the second difference;

in response to the product being zero, comparing the first difference to an equality threshold and comparing the second difference to the equality threshold; and increasing the count of the crossings of the notch filtered signal segment in response to the at least one of the first difference and the second difference being greater than the equality threshold.

23. The method of claim 16, wherein determining EMI is present in the cardiac signal segment comprises:

setting a threshold count value based on a ratio of an EMI frequency to be detected and a sampling rate of the cardiac signal segment;

comparing the value of the count to the threshold count value; and detecting EMI in the cardiac signal segment in response to the value of the count being equal to or greater than the threshold count value.

24. The method of claim 16, further comprising determining a frequency of the EMI based on the count of the crossings of the notch filtered signal segment in response to determining EMI is present in the cardiac signal segment.

25. The method of claim 16, further comprising:
receiving a second cardiac electrical signal by the sensing circuit via a second extra-cardiovascular sensing electrode vector different that the first extra-cardiovascular sensing electrode vector;
determining a morphology parameter from the second cardiac electrical signal in response to a cardiac event sensed by the sensing circuit from the first cardiac electrical signal;
comparing the morphology parameter to potential shockable beat criteria; and
determining that EMI is not present in the cardiac signal segment in response to the potential shockable beat criteria being satisfied.

26. The method claim 16, further comprising:
determining an EMI index in response to determining that EMI is present in the cardiac signal segment;
comparing the EMI index to alert criteria; and
generating an alert in response to the EMI index satisfying the alert criteria.

27. The method of claim 16, further comprising:
determining event intervals between consecutive cardiac events sensed by the sensing circuit;
comparing the event intervals to a tachyarrhythmia detection interval;
increasing a tachyarrhythmia interval count in response to each of one of the determined event intervals that is less than the tachyarrhythmia detection interval; and
determining the count of the crossings of the notch filtered signal segment by the cardiac signal segment in response to the tachyarrhythmia interval count being greater than a sensed event confirmation threshold.

28. The method of claim 16, further comprising:
updating an EMI event count in response to determining EMI is present in the cardiac signal segment;
determining event intervals between consecutive cardiac events sensed by the sensing circuit;
comparing the event intervals to a tachyarrhythmia detection interval;
increasing a tachyarrhythmia detection interval count in response to each one of the determined event intervals that is less than the tachyarrhythmia detection interval;
comparing the tachyarrhythmia detection interval count to a tachyarrhythmia detection threshold;
comparing the EMI event count to EMI detection criteria in response to the tachyarrhythmia detection interval count being equal to or greater than the tachyarrhythmia detection threshold; and
withholding detection of a tachyarrhythmia in response to the EMI event count satisfying the EMI detection criteria.

29. The method of claim 16, further comprising:
detecting a tachyarrhythmia from the first cardiac electrical signal; and
delivering the tachyarrhythmia therapy in response to detecting the tachyarrhythmia and determining that EMI is not present in the cardiac signal segment.

30. A non-transitory, computer-readable storage medium comprising a set of instructions which, when executed by a control circuit of an extra-cardiovascular implantable cardioverter defibrillator (ICD), cause the extra-cardiovascular ICD to:
receive a cardiac electrical signal via an extra-cardiovascular sensing electrode vector by a sensing circuit of the ICD;
sense a cardiac event by the sensing circuit in response to the cardiac electrical signal crossing a sensing threshold amplitude;
store a cardiac signal segment in memory of the ICD in response to the sensing circuit sensing the cardiac event;
obtain a notch filtered signal segment by notch filtering the cardiac signal segment;
determine a count of crossings of the notch filtered signal segment by the cardiac signal segment;
determine whether electromagnetic interference (EMI) is present in the cardiac signal segment based on a value of the count; and
withhold a tachyarrhythmia therapy in response to determining that EMI is present.

* * * * *